US008748108B2

(12) United States Patent (10) Patent No.: US 8,748,108 B2
McKeegan et al. (45) Date of Patent: Jun. 10, 2014

(54) BIOMARKERS FOR IDENTIFYING PATIENT CLASSES

(75) Inventors: Evelyn M. McKeegan, Lake Forest, IL (US); Barry L. Dowell, Mundelein, IL (US); Richard R. Lesniewski, Collegeville, PA (US); Dimitrí Semizarov, Chicago, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 13/311,752

(22) Filed: Dec. 6, 2011

(65) Prior Publication Data

US 2012/0178632 A1 Jul. 12, 2012

Related U.S. Application Data

(63) Continuation-in-part of application No. 13/309,307, filed on Dec. 1, 2011, which is a continuation of application No. 11/647,103, filed on Dec. 28, 2006, now abandoned.

(60) Provisional application No. 60/842,304, filed on Sep. 5, 2006.

(51) Int. Cl.
*G01N 33/53* (2006.01)
*A01N 61/00* (2006.01)

(52) U.S. Cl.
USPC .............................................. 435/7.1; 514/1

(58) Field of Classification Search
None
See application file for complete search history.

(56) References Cited

U.S. PATENT DOCUMENTS

| 5,091,513 | A | 2/1992 | Huston et al. |
| 5,447,841 | A | 9/1995 | Gray et al. |
| 5,491,224 | A | 2/1996 | Bittner et al. |
| 5,776,688 | A | 7/1998 | Bittner et al. |
| 2005/0272075 | A1 | 12/2005 | Jacobsen et al. |

FOREIGN PATENT DOCUMENTS

EP 1715041 A1 10/2006

OTHER PUBLICATIONS

Miyake et al (Cancer Research, Apr. 1994, 54:2136-2140).*
Oltersdorf et al (Nature, Jun. 2005 435:677-681).*
Shoemaker et al (Clinical Cancer Res, 2008, 14(11): 3268-3277).*
Nisman et al (Anticancer Research, 2009, 29(11): 4827-4832).*
Wu et al (J Thorac Oncol, 2009, 4(1): Abstract).*
Olejniczak et al (Mol Cancer Res, 2007, 5(4): 331-339).*
Etzioni et al (Nature Reviews, 2003, 3: pp. 1-10).*
Mercer (Immunol Ser, 1990, 53:39-54).*

Buck G.A., et al., "Design Strategies and Performance of Custom DNA Sequencing Primers," BioTechniques, 1999, 27 (3), 528-536.
Cimmino A., et al., "miR-15 and miR-16 Induce Apoptosis by Targeting BCL2," Proceedings of the National Academy of Sciences, 2005, vol. 102 (39), pp. 13944-13949.
Fan Y.S., "Molecular Cytogenetics" in: Methods In Molecular Biology, Humana Press, 2002, Table of Contents.
Galteland E., et al., "Translocation T(14;18) And Gain of Chromosome 18 1Bc12: Effects on Bcl2 Expression And Apoptosis In B-Cell Non-Hodgkins Lymphomas," Leukemia, 2005, vol. 19 (12), pp. 2313-2323.
Girard L., et al., "Genome-wide Allelotyping of lung Cancer Identifies New Regions of Allelic loss, Differences Between Small Cell lung Cancer and Non-small Cell lung Cancer, and Loci Clustering," Cancer Research, 2000, vol. 60 (17), pp. 4894-4906.
Haugland., et al., "Handbook of Fluorescent Probes and Research Chemicals," Molecular Probes, 1996, Table of Contents.
Hosoe S., et al., "A Frequent Deletion of Chromosome 5q21 in Advanced Small Cell and Non-small Cell Carcinoma of the Lung," Cancer Research, 1994, vol. 54 (7), pp. 1787-1790.
Hu Y., et al., "Antitumor Efficacy of Oblimersen Bcl-2 antisense Oligonucleotide Alone and in Combination with Vinorelbine in Xenograft Models of Human Non-small," Clinical Cancer Research, 2004, vol. 10 (22), pp. 7662-7670.
Huston J.S., et al., "Protein Engineering of Antibody Binding Sites: Recovery of Specific Activity in an Anti-Digoxin Single-Chain Fv Analogue Produced in *Escherichia Coli*," Proceedings of the National Academy of Sciences, 1988, vol. 85 (16), pp. 5879-5883.
International Preliminary Report on Patentability for Application No. PCT/US2007/026526, mailed on Oct. 11, 2011, 3 page.
International Search Report for Application No. PCT/US2007/026471, mailed on Sep. 5, 2008, 4 pages.
International Search Report for Application No. PCT/US2007/026526, mailed on Nov. 21, 2008, 7 pages.
Junker K., et al., "Pathology of Small-Cell Lung Cancer," Journal of Cancer Research and Clinical Oncology, 2000, vol. 126 (7), pp. 361-368.
Lebacq-Verheyden A.M., et al., "Human Gastrin-Releasing Peptide Gene Maps to Chromosome Band 18q21," Somatic Cell and Molecular Genetics, 1987, vol. 13 (1), pp. 81-86.
Levin n. A., et al., "Identification of Novel Regions of Altered DNA Copy Number In Small Cell lung Tumors," Genes, Chromosomes & Cancer, 1995, vol. 13 (3), pp. 175-185.
Martinez-Climent J.A., et al., "Transformation of Follicular Lymphoma to Diffuse Large Cell Lymphoma Is Associated With a Heterogeneous Set of Dnacopy Number and Gene Expression Alterations," Blood, 2003, vol. 101 (8), pp. 3109-3117.
Mattingly P.G., et al., In Instruments and Applications Luminescence: Instruments and Applications, Dyke K.V., Ed., CRC Press, 2002, pp. 77-105.
Monni O., et al., "BCL2 Overexpression Associated with Chromosomal Amplification in Diffuse Large B-cell Lymphoma," Blood, 1997, vol. 90 (3), pp. 1168-1174.

(Continued)

*Primary Examiner* — Sean Aeder
(74) *Attorney, Agent, or Firm* — Lisa V. Mueller; Michael Best & Friedrich LLP

(57) ABSTRACT

Disclosed are methods for classifying a patient with cancer as a candidate for therapy with a Bcl-2 family inhibitor comprising determining the level of at least one biomarker in a sample and comparing the biomarker level to a threshold level. Also described are methods for identifying classes of patients having a refractory cancer for second-line therapy comprising a Bcl-2 family inhibitor, where the method comprises determining the level of at least one biomarker in a sample and comparing the biomarker level to a threshold level.

9 Claims, 7 Drawing Sheets

(56) References Cited

OTHER PUBLICATIONS

Okusaka T., et al., "Serum Levels of Pro-gastrin-releasing Peptide for Follow-up of Patients With Small Cell Lung Cancer," Clinical Cancer Research, 1997, vol. 3 (1), pp. 123-127.

Peirson S.N., et al., "Experimental Validation of Novel and Conventional Approaches to Quantitative Real-time PCR Data Analysis," Nucleic Acids Research, 2003, vol. 31 (14), pp. E73.

Polak J.M., et al., Introduction to Immunocytochemistry, 2nd Edition, Springer-Verlag, 1997, Table of Contents.

Sasaki H., et al., "Elevated Serum Periostin Levels in Patients with Bone Metastases from Breast but not Lung Cancer," Breast Cancer Research and Treatment, 2003, vol. 77 (3), pp. 245-252.

Walch A.K., et al., "Typical and Atypical Carcinoid Tumors of the Lung are Characterized by 11q Deletions as Detected by Domparative Genomic Hybridization," The American Journal of Pathology, 1998, vol. 153 (4), pp. 1089-1098.

Werner C.A., et al., "High-level DNA Amplifications are Common Genetic Aberrations in B-cell Neoplasms," American Journal of Pathology, 1997, vol. 151 (2), pp. 335-342.

Written Opinion for Application No. PCT/US2007/026471, mailed on Sep. 5, 2008, 6 pages.

Yasui K., et al., "Alteration in Copy Numbers Of Genes as a Mechanism for Acquired Drug Resistance," Cancer Research, 2004, vol. 64 (4), pp. 1403-1410.

Zhao X., et al., "Homozygous Deletions and Chromosome Amplifications in Human Lung Carcinomas Revealed by Single Nucleotide Polymorphism Array Analysis," Cancer Research, 2005, vol. 65 (13), pp. 5561-5570.

* cited by examiner

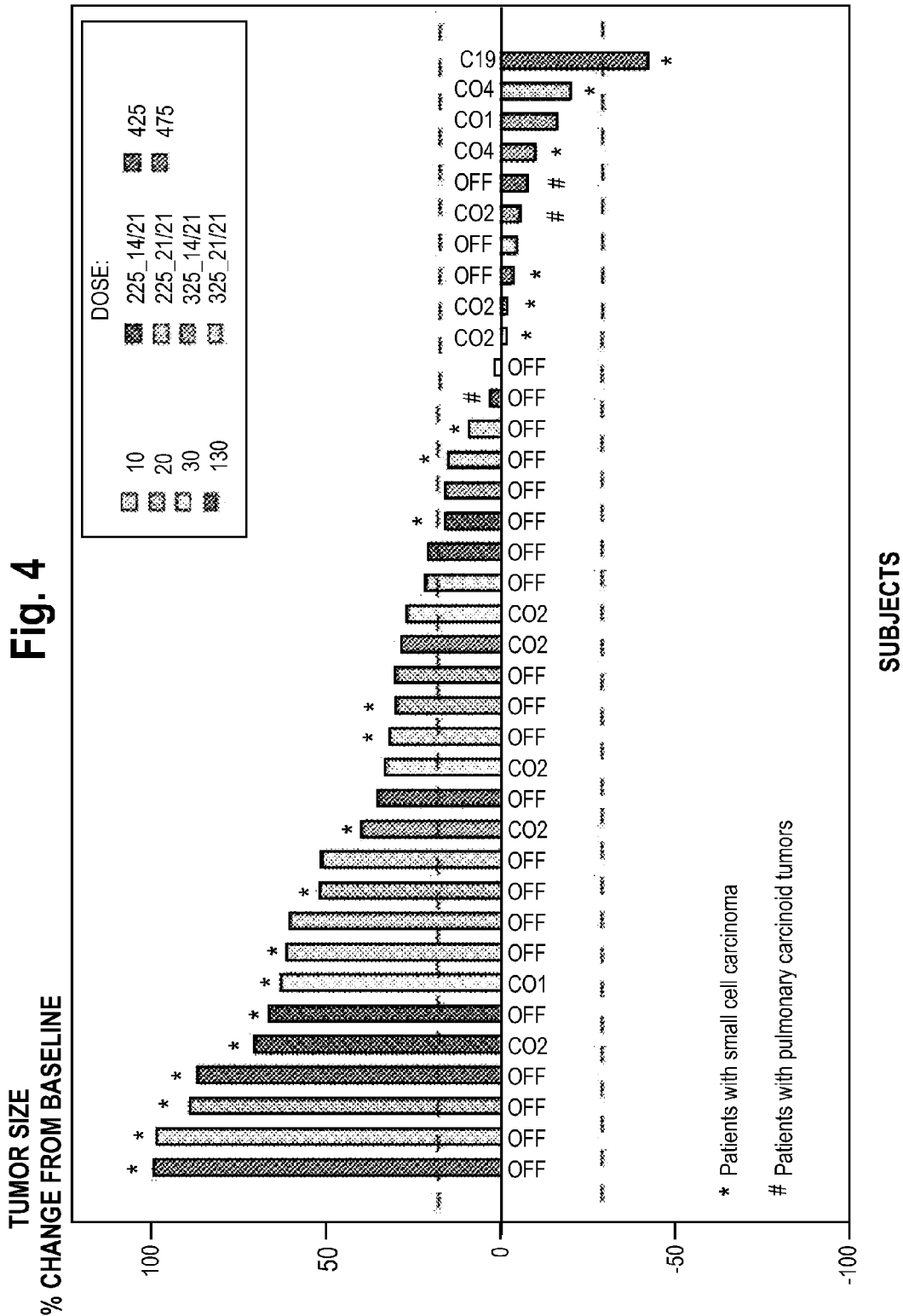

SEQUENCE LISTING

<160> NUMBER OF SEQ ID NOS: 24

<210> SEQ ID NO 1
<211> LENGTH: 24
<212> TYPE: DNA
<213> ORGANISM: Artificial Sequence
<220> FEATURE:
<223> OTHER INFORMATION: Primer sequence is synthesized.

<400> SEQUENCE: 1
tcctgagggt cttctctgtg gagg                                            24

<210> SEQ ID NO 2
<211> LENGTH: 24
<212> TYPE: DNA
<213> ORGANISM: Artificial Sequence
<220> FEATURE:

<223> OTHER INFORMATION: Primer sequence is synthesized.

<400> SEQUENCE: 2
tgtgcctgga atacatctcc gaga                                            24

<210> SEQ ID NO 3
<211> LENGTH: 29
<212> TYPE: DNA
<213> ORGANISM: Artificial Sequence
<220> FEATURE:
<223> OTHER INFORMATION: Primer sequence is synthesized

<400> SEQUENCE: 3
taagacagat caccttccaa gagagacac                                       29

<210> SEQ ID NO 4
<211> LENGTH: 23
<212> TYPE: DNA
<213> ORGANISM: Artificial Sequence
<220> FEATURE:
<223> OTHER INFORMATION: Primer sequence is synthesized

<400> SEQUENCE: 4
cacaggctgc actttagagg caa                                             23

<210> SEQ ID NO 5
<211> LENGTH: 25
<212> TYPE: DNA
<213> ORGANISM: Artificial Sequence
<220> FEATURE:
<223> OTHER INFORMATION: Primer sequence is synthesized

<400> SEQUENCE: 5
caacagcatg tgcttcatag ttgcc                                           25

<210> SEQ ID NO 6
<211> LENGTH: 27
<212> TYPE: DNA
<213> ORGANISM: Artificial Sequence
<220> FEATURE:
<223> OTHER INFORMATION: Primer sequence is synthesized

<400> SEQUENCE: 6
cgacagcact gcccactcta gtaatag                                         27

<210> SEQ ID NO 7
<211> LENGTH: 30
<212> TYPE: DNA
<213> ORGANISM: Artificial Sequence
<220> FEATURE:
<223> OTHER INFORMATION: Primer sequence is synthesized

<400> SEQUENCE: 7
aacaaacact tgaagacact gaagaacaac                                      30

<210> SEQ ID NO 8
<211> LENGTH: 28
<212> TYPE: DNA
<213> ORGANISM: Artificial Sequence
<220> FEATURE:
<223> OTHER INFORMATION: Primer sequence is synthesized

<400> SEQUENCE: 8
tgctctcaac tgaaaatggc tatatgtc                                        28

<210> SEQ ID NO 9

```
<211> LENGTH: 23
<212> TYPE: DNA
<213> ORGANISM: Artificial Sequence
<220> FEATURE:
<223> OTHER INFORMATION: Primer sequence is synthesized

<400> SEQUENCE: 9
tcttccaggg caccttactg tcc                                              23

<210> SEQ ID NO 10
<211> LENGTH: 20
<212> TYPE: DNA
<213> ORGANISM: Artificial Sequence
<220> FEATURE:
<223> OTHER INFORMATION: Primer sequence is synthesized

<400> SEQUENCE: 10
accagcaacc ccattccgag                                                  20

<210> SEQ ID NO 11
<211> LENGTH: 23
<212> TYPE: DNA
<213> ORGANISM: Artificial Sequence
<220> FEATURE:
<223> OTHER INFORMATION: Primer sequence is synthesized

<400> SEQUENCE: 11
ttgatgtgtc ccctgtgcct tta                                              23

<210> SEQ ID NO 12
<211> LENGTH: 29
<212> TYPE: DNA
<213> ORGANISM: Artificial Sequence
<220> FEATURE:
<223> OTHER INFORMATION: Primer sequence is synthesized

<400> SEQUENCE: 12
acaagttttt gcctctagat gacactgtt                                        29

<210> SEQ ID NO 13
<211> LENGTH: 26
<212> TYPE: DNA
<213> ORGANISM: Artificial Sequence
<220> FEATURE:
<223> OTHER INFORMATION: Primer sequence is synthesized

<400> SEQUENCE: 13
aacccgagga agtctaaatg aataat                                           26

<210> SEQ ID NO 14
<211> LENGTH: 26
<212> TYPE: DNA
<213> ORGANISM: Artificial Sequence
<220> FEATURE:
<223> OTHER INFORMATION: Primer sequence is synthesized

<400> SEQUENCE: 14
cacacccagt taccctgtt attaac                                            26

<210> SEQ ID NO 15
<211> LENGTH: 27
<212> TYPE: DNA
<213> ORGANISM: Artificial Sequence
<220> FEATURE:
<223> OTHER INFORMATION: Primer sequence is synthesized

<400> SEQUENCE: 15
```

-continued

```
tcctctctca tctgtagtct ggcttta                                          27

<210> SEQ ID NO 16
<211> LENGTH: 26
<212> TYPE: DNA
<213> ORGANISM: Artificial Sequence
<220> FEATURE:
<223> OTHER INFORMATION: Primer sequence is synthesized

<400> SEQUENCE: 16
aaactataat agcaatctgt gcccaa                                           26

<210> SEQ ID NO 17
<211> LENGTH: 20
<212> TYPE: DNA
<213> ORGANISM: Artificial Sequence
<220> FEATURE:
<223> OTHER INFORMATION: Primer sequence is synthesized

<400> SEQUENCE: 17
agcattggtg cgtgtggtgc                                                  20

<210> SEQ ID NO 18
<211> LENGTH: 25
<212> TYPE: DNA
<213> ORGANISM: Artificial Sequence
<220> FEATURE:
<223> OTHER INFORMATION: Primer sequence is synthesized

<400> SEQUENCE: 18
cctcttggtg gaatctagga tcagg                                            25

<210> SEQ ID NO 19
<211> LENGTH: 26
<212> TYPE: DNA
<213> ORGANISM: Artificial Sequence
<220> FEATURE:
<223> OTHER INFORMATION: Primer sequence is synthesized

<400> SEQUENCE: 19
ttcaagtgaa gttacctaat gctccc                                           26

<210> SEQ ID NO 20
<211> LENGTH: 26
<212> TYPE: DNA
<213> ORGANISM: Artificial Sequence
<220> FEATURE:
<223> OTHER INFORMATION: Primer sequence is synthesized

<400> SEQUENCE: 20
cctggggtac agaaatactt agtgat                                           26

<210> SEQ ID NO 21
<211> LENGTH: 26
<212> TYPE: DNA
<213> ORGANISM: Artificial Sequence
<220> FEATURE:
<223> OTHER INFORMATION: Primer sequence is synthesized

<400> SEQUENCE: 21
ttggaaagtc tggatgggaa tctttt                                           26

<210> SEQ ID NO 22
<211> LENGTH: 25
<212> TYPE: DNA
<213> ORGANISM: Artificial Sequence
<220> FEATURE:
```

```
<223> OTHER INFORMATION: Primer sequence is synthesized

<400> SEQUENCE: 22
aggggattta acctaccttt gtttc                                    25

<210> SEQ ID NO 23
<211> LENGTH: 26
<212> TYPE: DNA
<213> ORGANISM: Artificial Sequence
<220> FEATURE:
<223> OTHER INFORMATION: Primer sequence is synthesized

<400> SEQUENCE: 23
atgacaatta aattatcacg cttcca                                   26

<210> SEQ ID NO 24
<211> LENGTH: 26
<212> TYPE: DNA
<213> ORGANISM: Artificial Sequence
<220> FEATURE:
<223> OTHER INFORMATION: Primer sequence is synthesized

<400> SEQUENCE: 24
ttcttcttgt cagcagccac ttatca                                   26
```

BIOMARKERS FOR IDENTIFYING PATIENT CLASSES

CROSS-REFERENCE TO RELATED APPLICATION

This is a continuation-in-part of U.S. patent application Ser. No. 13/309,307, filed on Dec. 1, 2011, which is a continuation of U.S. patent application Ser. No. 11/647,103, filed Dec. 28, 2006, which claims priority to U.S. Provisional Patent Application No. 60/842,304, filed Sep. 5, 2006, the contents of all of which are fully incorporated herein by reference.

BACKGROUND OF THE INVENTION

Patients having recurrent, relapsed, or refractory cancers, such refractory metastatic small cell lung cancer (SCLC), are typically faced with a poor prognosis and few therapeutic options. For example, there are no FDA approved therapies for patients with chemorefractory SCLC, defined as progressive disease during or within 3 months after first line therapy, and the only therapy approved for use in the United States for recurrent SCLC is topotecan, which has a response rate of only 2-6% (Schiller, J. H., et al., Topotecan versus observation after cisplatin plus etoposide in extensive-stage small-cell lung cancer: E7593—a phase III trial of the Eastern Cooperative Oncology Group. J Clin Oncol 10:2114-22, 2001; von Pawel, J., et al., Topotecan versus cyclophosphamide, doxorubicin, and vincristine for the treatment of recurrent small-cell lung cancer. J Clin Oncol 17:658-67, 2007). Thus, there is a need for a diagnostic method to assess whether a patient having a cancer, and particularly a patient having recurrent, relapsed, or refractory cancer may derive a clinical benefit from a therapy.

Small molecule compounds, including ABT-737 and ABT-263, are inhibitors of the Bcl-2 family members Bcl-2, Bcl-XL, and Bcl-w, and have been shown to induce regression of solid tumors, Oltersdorf, T., "An inhibitor of Bcl-2 family proteins induces regression of solid tumours", Nature, 435: 677-681, 2005. ABT-737 has been tested against a diverse panel of human cancer cell lines and has displayed selective potency against SCLC and lymphoma cell lines, Ibid. ABT-737's chemical structure is provided by Oltersdorf et al. at p. 679.

Because of the potential therapeutic use of inhibitors for Bcl-2 family members, companion diagnostic assays are needed that are able to identify or classify patients, particularly patients having a refractive or recurring cancer, in order to indicate which candidate will benefit from treatment using Bcl-2 family inhibitor therapy. Additionally, there is a clear need to support this therapy with diagnostic assays using biomarkers that would classify cancer patients as candidates for, and facilitate monitoring the efficacy of, Bcl-2 family inhibition therapy.

SUMMARY OF THE INVENTION

In an aspect, the disclosure relates to a method for classifying a patient having cancer as a candidate for therapy with a Bcl-2 family inhibitor comprising: (a) providing a tissue, blood, serum or plasma sample from a patient; (b) determining the level of at least one of (i) plasma pro-gastrin releasing peptide (pro-GRP), (ii) cytokeratin 19 fragment antigen 21-1 (CYFRA 21-1), (iii) neuron-specific enolase (NSE), (iv) circulating tumor cell (CTC) number, (v) M30, (vi) M65, or (vii) Bcl-2 gene copy number in the sample; and (c) classifying the patient as a candidate for therapy with a Bcl-2 family inhibitor when the tissue, blood, serum or plasma sample is determined as having at least one of: an increased level, relative to a threshold level, of (i) plasma pro-gastrin releasing peptide (pro-GRP), (v) M30, (vi) M65, or (vii) Bcl-2 gene copy number; or a decreased level, relative to a threshold level, of at least one of (ii) cytokeratin 19 fragment antigen 21-1 (CYFRA 21-1), (iii) neuron-specific enolase (NSE), or (iv) circulating tumor cell (CTC) number; or any combination thereof.

In another aspect, the disclosure provides a method for classifying a patient having cancer as a candidate for second-line therapy with a Bcl-2 family inhibitor comprising: (a) providing a tissue, blood, serum or plasma sample from a patient; (b) determining the level of at least one of (i) plasma pro-gastrin releasing peptide (pro-GRP), (ii) cytokeratin 19 fragment antigen 21-1 (CYFRA 21-1), (iii) neuron-specific enolase (NSE), (iv) circulating tumor cell (CTC) number, (v) M30, (vi) M65, or (vii) Bcl-2 gene copy number in the sample; and (c) classifying the patient as a candidate for second-line therapy with a Bcl-2 family inhibitor when the tissue, blood, serum or plasma sample is determined as having at least one of: an increased level, relative to a threshold level, of (i) plasma pro-gastrin releasing peptide (pro-GRP), (v) M30, (vi) M65, or (vii) Bcl-2 gene copy number; or a decreased level, relative to a threshold level, of at least one of (ii) cytokeratin 19 fragment antigen 21-1 (CYFRA 21-1), (iii) neuron-specific enolase (NSE), or (iv) circulating tumor cell (CTC) number; or any combination thereof.

In some embodiments of the above aspects, the tissue, blood, serum or plasma sample is from a patient with a cancer selected from carcinoma, melanoma, lymphoma, blastoma, sarcoma, germ cell tumors, and leukemia or lymphoid malignancies. Some non-limiting examples of cancers include squamous cell cancer (e.g., epithelial squamous cell cancer), lung cancer including small-cell lung cancer, non-small cell lung cancer, adenocarcinoma of the lung and squamous carcinoma of the lung, esophageal cancer, prostate cancer, cancer of the peritoneum, hepatocellular cancer, gastric or stomach cancer including gastrointestinal cancer, neuroendocrine cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, melanoma, multiple myeloma and B-cell lymphoma, brain, as well as head and neck cancer, and associated metastases. In other embodiments, the tissue sample is from a patient with a relapsed or refractory cancer selected from the group consisting of small cell lung carcinoma (SCLC) and a solid tumor cancer. In some embodiments of the above aspects, (i) the plasma pro-GRP threshold level is about 600 pg/mL, (ii) the CYFRA 21-1 threshold level is about 2.3 ng/mL, (iii) the NSE threshold level is about 15 ng/mL, or (iv) the CTC number threshold level is about 12 per 7.5 mL.

In another aspect, the disclosure provides a reagent kit for an assay for classification of a patient for cancer therapy, such as eligibility for Bcl-2 inhibitor therapy, or for monitoring response to such therapy, comprising a container comprising at least one labeled antibody or protein capable of specific binding to one or more of: plasma pro-gastrin releasing peptide (pro-GRP), a pro-GRP precursor, or fragments thereof; cytokeratin 19 fragment antigen 21-1 (CYFRA 21-1); neuron-specific enolase (NSE), M30, M65, or a circulating tumor cell (CTC). In some embodiments, the reagent kits further comprise a calibration sample. In further embodiments, the reagent kits comprise instructions that provide a threshold level of at least one of (i) plasma pro-gastrin releasing peptide (pro-GRP), (ii) cytokeratin 19 fragment antigen 21-1 (CYFRA 21-1), (iii) neuron-specific enolase (NSE), (iv) circulating tumor cell (CTC) number, (v) M30, (vi) M65, or (vii) Bcl-2 gene copy number.

The disclosure provides capability for improving stratification of patients for Bcl-2 inhibitor therapy. The assessment of biomarker levels with the methods disclosed herein also allows tracking of individual patient response to the therapy using a readily obtainable patient sample. The methods have particular utility for treatment of SCLC, solid tumor cancers, and lymphoma patients with Bcl-2 inhibitors, for example ABT-737, ABT-263 or analogs thereof.

The disclosure also relates to other aspects and embodiments that will become apparent in light of the following detailed description.

BRIEF DESCRIPTION OF THE DRAWINGS

FIG. 4 shows best overall percentage change from baseline in target lesion measurement by RECIST guidelines for subjects at different dose levels.

DETAILED DESCRIPTION OF THE INVENTION

Figure 1:
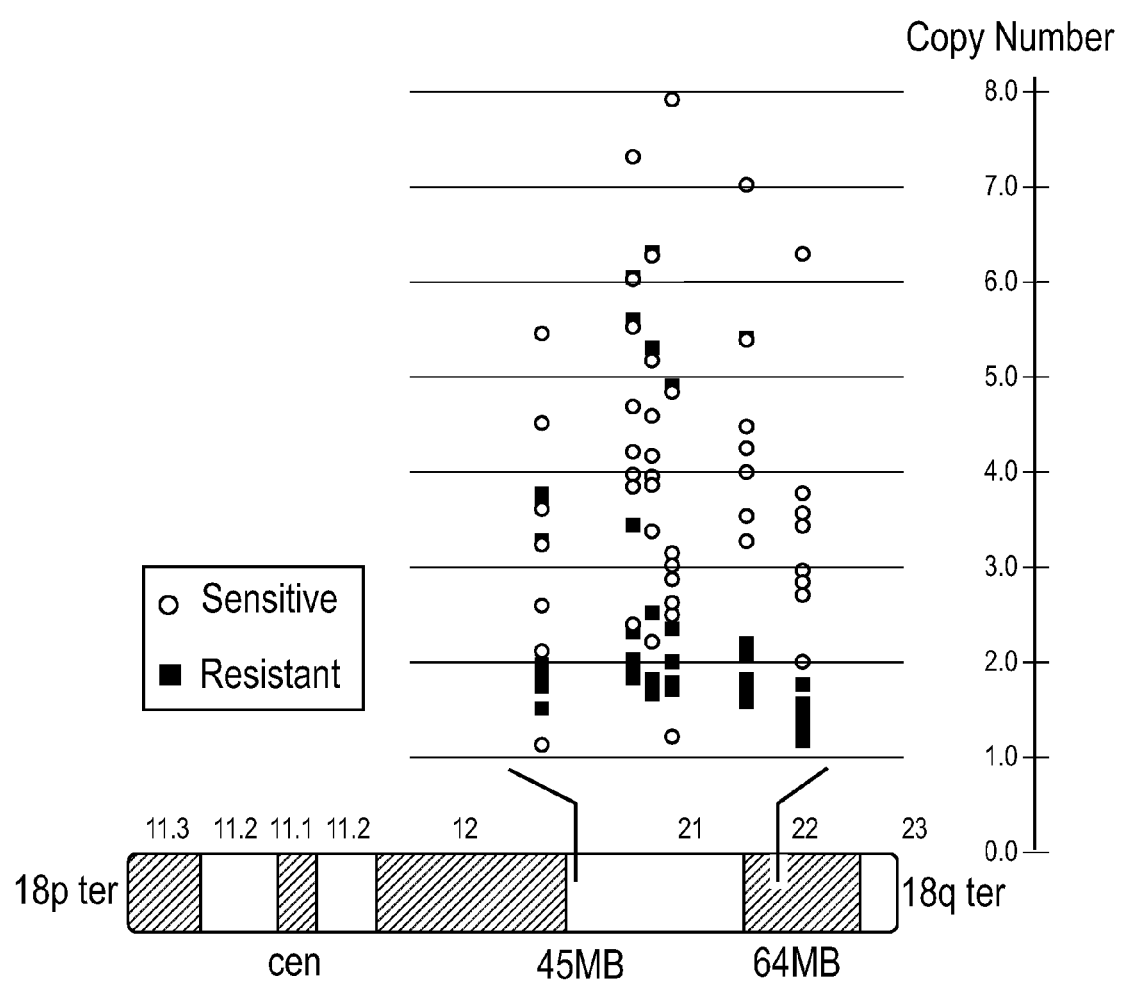
FIG. 1 shows a plot of experimental quantitative PCR determination of chromosomal copy number on chromosome arm 18q in various SCLC cell lines sensitive and resistant to ABT-737.

The present disclosure discusses the unexpected discovery that cancer patients can be classified on a scale regarding their ability to respond to particular cancer therapies through measurement of various biomarkers. The method includes the detection of at least one biomarker in a sample from a patient having cancer and comparing the level of biomarker in response to a particular therapeutic in comparison to a particular threshold level before treatment. In particular, this method is applicable to Bcl-inhibitor cancer therapies where a cancer candidate's biomarkers are measured and compared to a threshold level. The biomarkers may be pro-gastrin releasing peptide (pro-GRP), cytokeratin 19 fragment antigen 21-1 (CYFRA 21-1), neuron specific enolase (NSE), M30, M65, or circulating tumor cell (CTC). This method may be further applied to reducing the effects of particular therapeutic cancer drugs such as navitoclax, and can be used to treat patients of refractory or relapsed cancer.

DEFINITIONS

As used herein, an "antibody" refers to a protein consisting of one or more polypeptides substantially encoded by immunoglobulin genes or fragments of immunoglobulin genes. This term encompasses polyclonal antibodies, monoclonal antibodies, and fragments thereof, as well as molecules engineered from immunoglobulin gene sequences. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms "variable light chain (VL)" and "variable heavy chain (VH)" refer to these light and heavy chains respectively.

Antibodies exist as intact immunoglobulins or as a number of well-characterized fragments produced by digestion with various peptidases. Thus, for example, pepsin digests an antibody below the disulfide linkages in the hinge region to produce F(ab')2, a dimer of Fab which itself is a light chain joined to VH—CH1 by a disulfide bond. The F(ab')2 may be reduced under mild conditions to break the disulfide linkage in the hinge region thereby converting the (Fab').sub.2 dimer into a Fab' monomer. The Fab' monomer is essentially a Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology.

Thus, the term "antibody," as used herein also includes antibody fragments either produced by the modification of whole antibodies or synthesized de novo using recombinant DNA methodologies. Useful antibodies include single chain antibodies (antibodies that exist as a single polypeptide chain), more preferably single chain Fv antibodies (sFv or scFv), in which a variable heavy and a variable light chain are joined together (directly or through a peptide linker) to form a continuous polypeptide. The single chain Fv antibody is a covalently linked VH-VL heterodimer which may be expressed from a nucleic acid including VH— and VL-encoding sequences either joined directly or joined by a peptide-encoding linker. Huston, et al. (1988) Proc. Nat. Acad. Sci. USA, 85: 5879-5883. While the VH and VL are connected to each as a single polypeptide chain, the VH and VL domains associate non-covalently. The scFv antibodies and a number of other structures converting the naturally aggregated, but chemically separated, light and heavy polypeptide chains from an antibody V region into a molecule that folds into a three dimensional structure substantially similar to the structure of an antigen-binding site are known to those of skill in the art (see, e.g., U.S. Pat. Nos. 5,091,513, 5,132,405, and 4,956,778).

As used herein, a "Bcl-2 family inhibitor" refers to a therapeutic compound of any type, including small molecule-, antibody-, antisense-, small interfering RNA-, or microRNA-based compounds, that binds to at Bcl-2, and antagonizes the activity of the Bcl-2 related nucleic acid or protein. The methods are useful with any known or hereafter developed Bcl-2 inhibitor. One Bcl-2 inhibitor is ABT-737, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl) propyl)amino)-3-nitrobenzenesulfonamide, which binds to each of Bcl-2, Bcl-XL, and Bcl-w. Another Bcl-2 inhibitor is ABT-263, N-(4-(4-(2-(4-chlorophenyl)-5,5-dimethyl-1-cyclohex-1-en-1-yl)methyl)pip-erazin-1-yl)benzoyl)-4-(((1R)-3-(morpholin-4-yl)-1-((phenylsulfanyl)methyl) propyl) amino)-3-((trifluoromethyl)sulfonyl)benzenesulfonamide.

The chemical structure of ABT-263 is:

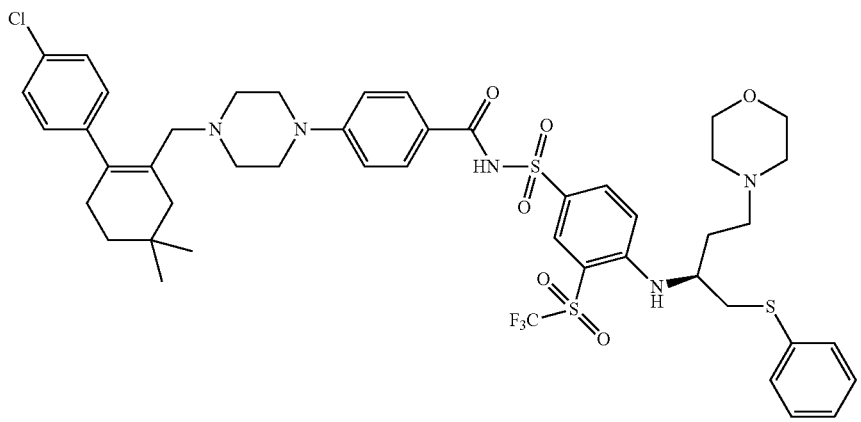 [SMILES: CC1(C)CCC(c2ccc(Cl)cc2)=C(CN2CCN(c3ccc(C(=O)NS(=O)(=O)c4ccc(N[C@@H](CCN5CCOCC5)CSc5ccccc5)c(S(=O)(=O)C(F)(F)F)c4)cc3)CC2)C1]

The chemical structure of ABT-737 is:

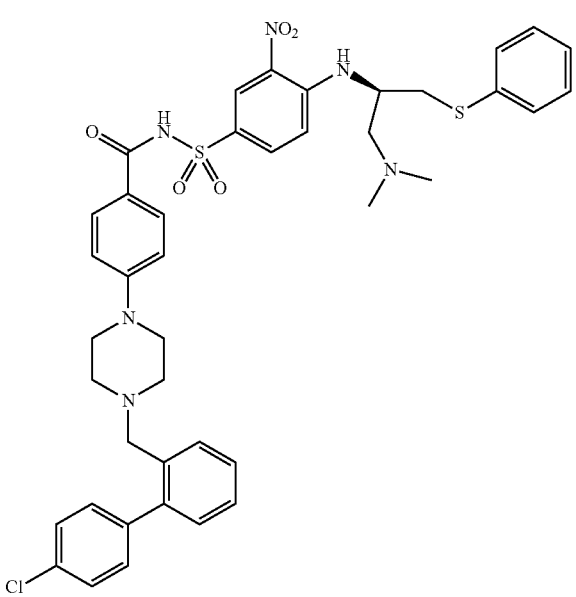 [SMILES: CN(C)C[C@H](CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-]]

In some embodiments, the method provides for selection of patients eligible for therapy with analogs of either ABT-737 or ABT-263.

"Therapeutic" as used herein relates broadly to any agent or treatment that can inhibit, slow, or halt progression or proliferation of a cancer cell, cause apoptosis of a cancer cell, induce remission of disease, or provide prophylaxis of or reduce the number and/or severity of symptoms associated with cancer (i.e., provides a degree of clinical benefit to a cancer patient).

I) Method of Classifying a Cancer Patient for a Therapeutic Regimen

In a general sense, the disclosure relates to a method of classifying a patient having cancer as a candidate for treatment with a therapeutic. The method includes detecting at least one biomarker in a sample from a patient having cancer and comparing the level of the biomarker to a threshold level for the biomarker and using a difference in the levels to classify the patient as a good candidate for therapy.

The method may be for classifying a patient having cancer as a candidate for therapy with a Bcl-2 family inhibitor or combination therapy thereof. The method may comprise providing a tissue, blood, serum or plasma sample from a patient having cancer, determining the level of at least one biomarker in the tissue, blood, serum or plasma sample, and classifying the patient as a candidate for therapy with a Bcl-2 family inhibitor when the tissue, blood, serum or plasma sample is determined as having an increased or decreased level relative to the threshold level of at least one of the biomarkers.

The method can be used for targeted cancer therapy. In particular, the method is useful for therapy selection for patients having small cell lung cancer and solid tumor cancers, such as therapy with a therapeutic such as a Bcl-2 family (e.g., Bcl-2) inhibitor. The method can be used as companion assays for Bcl-2 family inhibitor therapy, given either as monotherapy or as part of combination therapy with another therapy or therapeutic, such as conventional chemotherapy or radiation therapy. The method can be performed in relation to any cancer type in which at least one biomarker is increased or decreased relative to a threshold level of the biomarker. Other examples of such cancers can include carcinoma, melanoma, lymphoma, blastoma, sarcoma, germ cell tumors, and leukemia or lymphoid malignancies, such as, for example squamous cell cancer (e.g., epithelial squamous cell cancer), lung cancer including small-cell lung cancer, non-small cell lung cancer, adenocarcinoma of the lung and squamous carcinoma of the lung, esophageal cancer, prostate cancer, cancer of the peritoneum, hepatocellular cancer, gastric or stomach cancer including gastrointestinal cancer, neuroendocrine cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, melanoma, multiple myeloma and B-cell lymphoma, brain, as well as head and neck cancer, and associated metastases.

The method may be used for classifying a patient having cancer as a candidate for second-line therapy with a therapeutic such as a Bcl-2 family inhibitor. In some embodiments, the patient is selected based on lack of success of one or more prior therapies. The method can be used to assess the viability and provide a prognostic evaluation of whether a patient having a cancer that has been resistant to prior therapies may be successfully treated with a therapy comprising a Bcl-2 family inhibitor. The method can be used for targeted cancer therapy selection for patients having a refractory, recurrent, or relapsed cancer such as, for example, small cell lung cancer and solid tumor cancers, such as therapy with Bcl-2 family (e.g., Bcl-2) inhibitors. The method can be used as companion assays for Bcl-2 family inhibitor therapy, given either as monotherapy or as part of combination therapy with another therapy or therapeutic, such as conventional chemotherapy or radiation therapy. The method can be performed in relation to any refractory, recurrent, or relapsed cancer type in which at least one biomarker is increased or decreased relative to a threshold level of the biomarker. Other examples of such refractory, recurrent, or relapsed cancers can include can include carcinoma, melanoma, lymphoma, blastoma, sarcoma, germ cell tumors, and leukemia or lymphoid malignancies, such as, for example squamous cell cancer (e.g., epithelial squamous cell cancer), lung cancer including small-cell lung cancer, non-small cell lung cancer, adenocarcinoma of the lung and squamous carcinoma of the lung, esophageal cancer, prostate cancer, cancer of the peritoneum, hepatocellular cancer, gastric or stomach cancer including gastrointestinal cancer, neuroendocrine cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, melanoma, multiple myeloma and B-cell lymphoma, brain, as well as head and neck cancer, and associated metastases.

The dosage of the Bcl-2 inhibitor can vary based on any variety of factors known in the art (e.g., patient health, age, weight, gender, cancer type, stage/progression of cancer, etc.), and can be readily determined by one of skill. In some embodiments the Bcl-2 inhibitor can be administered to a patient in an amount of 10 mg/day-500 mg/day, about 10 mg/day to about 200 mg/day (e.g., 10, 20, 30, 40, 50, 60, 70, 80, 90, 100, 110, 120, 130, 140, 150, 160, 170, 180, 190, or 200 mg/day), 100 mg/day to about 200 mg/day, or about 200 mg/day to about 500 mg/day (e.g., 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 mg/day), inclusive of any single or multi-dose daily administration regimen that falls within that total daily dose range. In some embodiments, the dose is from 150-325 mg/day.

The assays can identify a biomarker for both predicting therapy response and for monitoring patient response to a therapeutic regimen such as Bcl-2 family inhibitor therapy. Assays for response prediction are run before start of therapy and patients showing levels of a biomarker above or below a threshold level of the biomarker are eligible to receive Bcl-2 family inhibitor therapy. For monitoring patient response, the assay is run at the initiation of therapy to establish baseline levels of the biomarker in the tissue, blood, serum or plasma sample, for example, the percent of total cells or number of cells showing the copy number gain in the sample. The same tissue, blood, serum or plasma is then sampled and assayed and the levels of the biomarker compared to the baseline. The biomarker level can indicate that the therapy is likely being effective and can be continued or if the patient may not be responding to therapy. The baseline level can be determined in a peripheral blood sample taken from the patient at the time of start of therapy.

The method uses observable differences between the level of a biomarker in a sample from a patient and a threshold level for the biomarker to classify the patient as a good candidate for therapy. In some embodiments, a patient sample having a biomarker level below the threshold level indicates that the patient is a candidate for Bcl-2 family inhibitor therapy. In some embodiments, a patient sample having a biomarker level above the threshold level indicates that the patient is a candidate for Bcl-2 family inhibitor therapy. In some embodiments, a combination of biomarker levels (e.g., determining the level of two or more biomarkers from a patient sample) can be used to evaluate and classify the patient is a candidate for Bcl-2 family inhibitor therapy. In some embodiments, a threshold level for a particular biomarker in a particular type of cancer may be more indicative that the patient is a candidate for Bcl-2 family inhibitor therapy relative to another biomarker. Threshold levels can vary depending on the particular biomarker and can be determined by any appropriate method such as statistical evaluation of data (e.g., using software such as JMP 8.0, BATTing (Bootstrapping and Aggregating Thresholds from Trees) method, R statistical software, etc.). Threshold levels can be determined using biomarker data from a pool of patients having similar cancer type (e.g., solid tumors), the same cancer type (e.g., SCLC), cancer that is recurrent, refractory, or relapsed, or cancers that are treated with a particular therapeutic (e.g., platinum-based therapy).

Depending on the biomarker, appropriate threshold levels range from 1.5 ng/mL to 4 ng/mL, 10 ng/mL to 20 ng/mL, 5 cell counts/7.5 mL to 20 cell counts/7.5 mL, 500 pg/mL to 700 pg/mL, normal copy numbers of a gene, or are baseline levels of markers established prior to or during therapy.

A) Detection of Biomarkers

The method measures the level of biomarker to compare to a threshold level. The biomarker can be measured in a number of different ways.

1. Chromosome Copy Number Change.

The biomarker may be measured by evaluating a chromosome copy number change at a chromosome locus of a biomarker. Genomic biomarkers can be identified by any technique such as, for example, comparative genomic hybridization (CGH), or by single nucleotide polymorphism arrays (genotyping microarrays) of cell lines, such as cancer cells. A bioinformatics approach can identify regions of chromosomal aberrations that discriminate between cell line groups and that are indicative of the biomarker, using appropriate copy number thresholds for amplifications and deletions in addition to further analysis using techniques such as qPCR or in situ hybridization.

Nucleic acid assay methods for detection of chromosomal DNA copy number changes include: (i) in situ hybridization assays to intact tissue or cellular samples, (ii) microarray hybridization assays to chromosomal DNA extracted from a tissue sample, and (iii) polymerase chain reaction (PCR) or other amplification assays to chromosomal DNA extracted from a tissue sample. Assays using synthetic analogs of nucleic acids, such as peptide nucleic acids, in any of these formats can also be used.

2. Hybridization/PCR of Genetic Biomarkers.

The biomarker may be detected through hybridization of PCT of nucleic acids encoding the biomarker. Detection of the genomic biomarkers is done by hybridization assays using detectably labeled nucleic acid-based probes, such as deoxyribonucleic acid (DNA) probes or protein nucleic acid (PNA) probes, or unlabeled primers which are designed/selected to hybridize to the specific designed chromosomal target. The unlabeled primers are used in amplification assays, such as by polymerase chain reaction (PCR), in which after primer binding, a polymerase amplifies the target nucleic acid sequence for subsequent detection. The detection probes used in PCR or other amplification assays are preferably fluorescent, and still more preferably, detection probes useful in "real-time PCR". Fluorescent labels are also preferred for use in situ hybridization but other detectable labels commonly used in hybridization techniques, e.g., enzymatic, chromogenic and isotopic labels, can also be used. Useful probe labeling techniques are described in Molecular Cytogenetics: Protocols and Applications, Y.-S. Fan, Ed., Chap. 2, "Labeling Fluorescence In Situ Hybridization Probes for Genomic Targets", L. Morrison et al., p. 21-40, Humana Press,© 2002, incorporated herein by reference. In detection of the genomic biomarkers by microarray analysis, these probe labeling techniques are applied to label a chromosomal DNA extract from a patient sample, which is then hybridized to the microarray.

In situ hybridization is used to detect the presence of chromosomal copy number increase or gene amplification at a biomarker locus. Probes for use in the in situ hybridization methods of the invention fall into two broad groups: chromosome enumeration probes, i.e., probes that hybridize to a chromosomal region, usually a repeat sequence region, and indicate the presence or absence of an entire chromosome, and locus specific probes, i.e., probes that hybridize to a specific locus on a chromosome and detect the presence or absence of a specific locus. It is preferred to use a locus specific probe that can detect changes of the unique chromosomal DNA sequences at the interrogated locus. Methods for use of unique sequence probes for in situ hybridization are described in U.S. Pat. No. 5,447,841, incorporated herein by reference.

A chromosome enumeration probe can hybridize to a repetitive sequence, located either near or removed from a centromere, or can hybridize to a unique sequence located at any position on a chromosome. For example, a chromosome enumeration probe can hybridize with repetitive DNA associated with the centromere of a chromosome. Centromeres of primate chromosomes contain a complex family of long tandem repeats of DNA comprised of a monomer repeat length of about 171 base pairs that are referred to as alpha-satellite DNA. Centromere fluorescence in situ hybridization probes to each of chromosomes 14 and 18 are commercially available from Abbott Molecular (Des Plaines, Ill.).

In situ hybridization probes employ directly labeled fluorescent probes, such as described in U.S. Pat. No. 5,491,224, incorporated herein by reference. U.S. Pat. No. 5,491,224 also describes simultaneous FISH assays using more than one fluorescently labeled probe. Use of a pair of fluorescent probes, for example, one for the a biomarker and one for the centromere of a chromosome on which it is located, allows determination of the ratio of the gene locus copy number to the centromere copy number. This multiplex assay can provide a more precise identification of copy number increase through determination on a cell-by-cell basis of whether gene amplification, ie. a ratio of the number of the gene locus probe signals to the centromere probe signals in each cell that is greater than 2, exists, or whether gain of the entire chromosome has occurred, ie. a ratio of the number of the gene locus probe signals to the centromere probe signals in each cell of 1/1 to less than 2/1, but with more than the normal number of two gene locus probe signals. Samples that are classified as amplified from dual probe analysis with ratios of 2/1 or greater, or those having three or more gene locus probe signals, either in dual probe or single probe analysis, are identified as having the chromosomal gain related to Bcl-2 family inhibitor therapy.

Useful locus specific probes can be of any desired length and produced in any manner and will generally contain sequences to hybridize to a chromosomal DNA target sequence of about 10,000 to about 1,000,000 bases long. Preferably the probe will hybridize to a target stretch of chromosomal DNA at the target locus of at least 100,000 bases long to about 500,000 bases long, and will also include unlabeled blocking nucleic acid in the probe mix, as disclosed in U.S. Pat. No. 5,756,696, herein incorporated by reference, to avoid non-specific binding of the probe. It is also possible to use unlabeled, synthesized oligomeric nucleic acid or peptide nucleic acid as the blocking nucleic acid or as the centromeric probe. For targeting the particular gene locus, it is preferred that the probes include nucleic acid sequences that span the gene and thus hybridize to both sides of the entire genomic coding locus of the gene. The probes can be produced starting with human DNA containing clones such as Bacterial Artificial Chromosomes (BAC's) or the like. BAC libraries for the human genome are available from Invitrogen and can be investigated for identification of useful clones. The University of California Santa Cruz Genome Browser can be used to identify DNA sequences in the target locus. These DNA sequences can then be used to identify useful clones contained in commercially available or academic libraries. The clones can then be labeled by conventional nick translation methods and tested as in situ hybridization probes.

Examples of fluorophores that can be used in the in situ hybridization methods described herein are: 7-amino-4-methylcoumarin-3-acetic acid (AMCA), Texas Red™ (Molecular Probes, Inc., Eugene, Oreg.); 5-(and -6)-carboxy-X-rhodamine, lissamine rhodamine B, 5-(and -6)-carboxyfluorescein; fluorescein-5-isothiocyanate (FITC); 7-diethylaminocoumarin-3-carboxylic acid, tetramethylrhodamine-5-(and -6)-isothiocyanate; 5-(and -6)-carboxytetramethylrhodamine; 7-hydroxy-coumarin-3-carboxylic acid; 6-[fluorescein 5-(and -6)-carboxamido]hexanoic acid; N-(4, 4-difluoro-5,7-dimethyl-4-bora-3a,4a diaza-3-indacenepropionic acid; eosin-5-isothiocyanate; erythrosine-5-isothiocyanate; 5-(and -6)-carboxyrhodamine 6G; and Cascade™ blue aectylazide (Molecular Probes).

Probes can be viewed with a fluorescence microscope and an appropriate filter for each fluorophore, or by using dual or triple band-pass filter sets to observe multiple fluorophores. See, e.g., U.S. Pat. No. 5,776,688 to Bittner, et al., which is incorporated herein by reference. Any suitable microscopic imaging method can be used to visualize the hybridized probes, including automated digital imaging systems, such as those available from MetaSystems, Zeiss, Bioview, or Applied Imaging. Alternatively, techniques such as flow cytometry can be used to examine the hybridization pattern of the chromosomal probes.

Although a cell-by-cell copy number analysis results from in situ hybridization, the genomic biomarkers can also be determined by quantitative PCR. In this method, chromosomal DNA is extracted from the tissue sample, and is then amplified by PCR using a pair of primers specific to at least one biomarker, or by multiplex PCR, using multiple pairs of primers. Any primer sequence for the biomarkers can be used. The copy number of the tissue is then determined by comparison to a reference amplification standard, Microarray copy number analysis can also be used. The chromosomal DNA after extraction is labeled for hybridization to a microarray comprising a substrate having multiple immobilized unlabeled nucleic acid probes arrayed at probe densities up to several million probes per square centimeter of substrate surface. Multiple microarray formats exist and any of these can be used, including microarrays based on BAC's and on oligonucleotides, such as those available from Agilent Technologies (Palo Alto, Calif.), and Affymetrix (Santa Clara, Calif.). When using a oligonucleotide microarray to detect chromosomal copy number change, it is preferred to use a microarray that has probe sequences to more than three separate locations in the targeted region.

3. Immunoassays and Protein Assays.

The biomarker protein may be detected though immunological means or other protein assays. Protein assay methods useful in the invention to measure biomarker levels may comprise (i) immunoassay methods involving binding of a labeled antibody or protein to the expressed biomarker, (ii) mass spectrometry methods to determine expressed biomarker, and (iii) proteomic based or "protein chip" assays for the expressed biomarker. Useful immunoassay methods include both solution phase assays conducted using any format known in the art, such as, but not limited to, an ELISA format, a sandwich format, a competitive inhibition format (including both forward or reverse competitive inhibition assays) or a fluorescence polarization format, and solid phase assays such as immunohistochemistry (referred to as "IHC").

An embodiment of an immunoassay is sandwich type format, wherein antibodies are employed to separate and quantify biomarker levels in the test sample or test sample extract. More specifically, at least two antibodies bind to different parts of the biomarker, forming an immune complex which is referred to as a "sandwich". Generally, one or more antibodies can be used to capture the biomarker target in the test sample (these antibodies are frequently referred to as a "capture" antibody or "capture" antibodies) and one or more antibodies is used to bind a detectable (namely, quantifiable) label to the sandwich (these antibodies are frequently referred to as the "detection" antibody or antibodies). In a sandwich assay, it is preferred that both antibodies binding to the target are not diminished by the binding of any other antibody in the assay to its respective binding site. In other words, antibodies should be selected so that the one or more first antibodies brought into contact with a test sample or test sample extract do not bind to all or part of the binding site recognized by the second or subsequent antibodies, thereby interfering with the ability of the one or more second detection antibodies to bind. In a sandwich assay, the antibodies, suitably, the at least one capture antibody, are used in molar excess amounts of the maximum amount of biomarker expected in the test sample or test sample extract. For example, from about 5 µg/mL to about 1 mg/mL of antibody per mL of solid phase containing solution can be used.

Any suitable antibodies or binding proteins that bind to a biomarker can be used. Monoclonal antibodies are preferred, and a number of suitable ELISA assay kits for various biomarkers are available from a variety of commercial sources. The biomarker-antibody/protein immune complexes formed in these assays can be detected using any suitable technique. Any suitable label can be used. The selection of a particular label is not critical, but the chosen label must be capable of producing a detectable signal either by itself or in conjunction with one or more additional substances.

Useful detectable labels, their attachment to antibodies and detection techniques therefore are known in the art. Any detectable label known in the art can be used. For example, the detectable label can be a radioactive label, such as, $^{3}H$, $^{125}I$, $^{35}S$, $^{14}C$, $^{32}P$, $^{33}P$, an enzymatic label, such as horseradish peroxidase, alkaline peroxidase, glucose 6-phosphate dehydrogenase, etc., a chemiluminescent label, such as, acridinium derivatives, luminol, isoluminol, thioesters, sulfonamides, phenanthridinium esters, etc. a fluorescence label, such as, fluorescein (5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, etc.), rhodamine, phycobiliproteins, R-phycoerythrin, quantum dots (zinc sulfide-capped cadmium selenide), a thermometric label or an immuno-polymerase chain reaction label. An introduction to labels, labeling procedures and detection of labels is found in Polak and Van Noorden, Introduction to Immunocytochemistry, 2.sup.nd ed., Springer Verlag, N.Y. (1997) and in Haugland, Handbook of Fluorescent Probes and Research Chemi (1996), which is a combined handbook and catalogue published by Molecular Probes, Inc., Eugene, Oreg., each of which is incorporated herein by reference. Preferred labels for use with the invention are chemiluminscent labels such as acridinium-9-carboxamide. Additional detail can be found in Mattingly, P. G., and Adamczyk, M. (2002) Chemiluminescent N-sulfonylacridinium-9-carboxamides and their application in clinical assays, in Luminescence Biotechnology: Instruments and Applications (Dyke, K. V., Ed.) pp 77-105, CRC Press, Boca Raton.

The detectable label can be bound to the analyte or antibody either directly or through a coupling agent. An example of a coupling agent that can be used is EDAC (1-ethyl-3-(3-dimethylaminopropyl) carbodiimide, hydrochloride) that is commercially available from Sigma-Aldrich (St. Louis, Mo.). Other coupling agents that can be used are known in the art. Methods for binding a detectable label to an antibody are known in the art. Additionally, many detectable labels can be purchased or synthesized that already contain end groups that facilitate the coupling of the detectable label to the antibody, such as, N10-(3-sulfopropyl)-N-(3-carboxypropyl)-acridinium-9-carboxamide, otherwise known as CPSP-Acridinium Ester or N10-(3-sulfopropyl)-N-(3-sulfopropyl)-acridinium-9-carboxamide, otherwise known as SPSP-Acridinium Ester.

The capture antibody can be bound to a solid support which facilitates the separation of the antibody-biomarker complex from the test sample. The type of solid support or "solid phase" used in the immunoassay is not critical and can be selected by one skilled in the art. A solid phase or solid support, as used herein, refers to any material that is insoluble, or can be made insoluble by a subsequent reaction. Useful solid phases or solid supports are known to those in the art and include the walls of wells of a reaction tray, test tubes, polystyrene beads, magnetic beads, nitrocellulose strips, membranes, microparticles such as latex particles, sheep (or other animal) red blood cells, and Duracytes® (a registered trademark of Abbott Laboratories, Abbott Park, Ill.), which are red blood cells "fixed" by pyruvic aldehyde and formaldehyde, and others. Suitable methods for immobilizing peptides on solid phases include ionic, hydrophobic, covalent interactions and the like. The solid phase can be chosen for its intrinsic ability to attract and immobilize the capture reagent. Alternatively, the solid phase can comprise an additional receptor which has the ability to attract and immobilize the capture reagent. The additional receptor can include a charged substance that is oppositely charged with respect to the capture reagent itself or to a charged substance conjugated to the capture reagent.

After the test sample or test sample extract is brought into contact with the capture antibody, the resulting mixture is incubated to allow for the formation of a first capture antibody-biomarker complex. The incubation can be carried out at any suitable pH, including a pH of from about 4.5 to about 10.0, at any suitable temperature, including from about 2° C. to about 45° C., and for a suitable time period from at least about one (1) minute to about eighteen (18) hours, and preferably from about 4-20 minutes.

After formation of the labeled complex, the amount of label in the complex is quantified using techniques known in the art. For example, if an enzymatic label is used, the labeled complex is reacted with a substrate for the label that gives a quantifiable reaction such as the development of color. If the label is a radioactive label, the label is quantified using a scintillation counter. If the label is a fluorescent label, the label is quantified by stimulating the label with a light of one color (which is known as the "excitation wavelength") and detecting another color (which is known as the "emission wavelength") that is emitted by the label in response to the stimulation. If the label is a chemiluminescent label, the label is quantified detecting the light emitted either visually or by using luminometers, x-ray film, high speed photographic film, a CCD camera, etc. For solution phase immunoassays, once the amount of the label in the complex has been quantified, the concentration of biomarker in the test sample is determined by use of a standard curve that has been generated using serial dilutions of the biomarker of known concentration. Other than using serial dilutions of the biomarker, the standard curve can be generated gravimetrically, by mass spectroscopy and by other techniques known in the art.

For IHC assays for a biomarker, detection of the antibody-antigen binding is preferably done using a conjugated enzyme label attached to a secondary binding antibody, such as horseradish peroxidase. These enzymes in the presence of colored substrate, produce at the site of the binding a colored deposit, called the stain, which can be identified under a light microscope. The site and extent of the staining is then identified and classified. In addition to manual inspection of the slide, automated IHC imaging techniques are known to the art and can be used.

B) Biomarkers

1. CYFRA 21-1.

The biomarker of the method may be cytokeratin 19 fragment antigen 21-1 (CYFRA 21-1). Cytokeratin 19 fragment antigen 21-1 (CYFRA 21-1) is a soluble fragment of human keratin, type I cytoskeletal 19 protein (or "cytokeratin-19," "CK-19," "keratin-19," "K19") encoded by the KRT19 gene. While it is expressed in all body fluids, it is primarily found in the lung, with levels rising in response to epithelial cell-associated carcinomas. Thus, CYFRA 21-1 can be used as a marker (typically detected using monoclonal antibodies BM19.21 and KS19.1) for treatment monitoring and prognosis of some cancers, and a number of commercially available assays are available for its detection (e.g., ARCHITECT ELISA kits (Abbott Diagnostics, Abbott Park, Ill.). Standard assays for detecting CYFRA 21-1 typically span a range of 0 ng/mL to about 100 ng/mL.

A correlation exists between plasma levels of CYFRA 21-1 in samples taken from cancer patients and clinical benefit of a therapy comprising a Bcl-2 family inhibitor. Thus, in some embodiments of the method disclosed herein, a decreased level, relative to a threshold level, of cytokeratin 19 fragment antigen 21-1 (CYFRA 21-1) identifies a patient as a candidate for Bcl-inhibitor therapy. The threshold level can range from about 1.5-4 ng/mL (e.g., 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4.0 ng/mL). Suitably, the threshold level is about 2.0-2.5 ng/mL. In some embodiments the threshold level is 2.3 ng/mL. A decreased level of CYFRA 21-1 in a sample can be any detectable difference between the sample measurement and the threshold level where the sample level of CYFRA21-1 is less than the threshold (e.g., from 1% to over 100% lower).

2. NSE.

The biomarker of the method may be neuron-specific enolase (NSE). Neuron-specific enolase (NSE) ("gamma-enolase," "2-phospho-D-glycerate hydro-lyase," "enolase 2," "ENO2," or "neural enolase") is an phosphopyruvate hydratase that is encoded by the human ENO2 gene. NSE is produced by small cell carcinomas which are neuroendocrine in origin, and can be used as a tumor marker for patients with some lung cancers (typically using NSE antibodies). NSE can be measured using any known technique, such as by automated electrochemoluminescent assays (e.g., Elecsys 2010 (Roche Diagnostics, Germany) or ARCHITECT ELISA kits (Abbott Diagnostics, Abbott Park, Ill.).

In some embodiments of the method disclosed herein, a decreased level, relative to a threshold level, of NSE identifies a patient as a candidate for Bcl-2 family inhibitor therapy. The threshold level can range from about 10-20 ng/mL (e.g., 10, 11, 12, 13, 14, 15, 16, 17, 18, 19, or 20 ng/mL). Suitably, the threshold level is about 15 ng/mL. A decreased level of NSE in a sample can be any detectable difference between the sample measurement and the threshold level where the sample level of NSE is less than the threshold (e.g., from 1% to over 100% lower).

3. CTC.

The biomarker of the method may be circulating tumor cells (CTCs). Circulating tumor cells (CTCs) are cells that have detached from a primary tumor and circulate in the bloodstream and are often indicative of tumor metastasis in different tissues. The detection of CTCs may have important prognostic and therapeutic implications but because their numbers can be very small, these cells are not easily detected. Typically, CTCs are found in frequencies in the order of 1-100 CTC per mL of whole blood in patients with metastatic disease. This low frequency of CTC in blood typically requires that methods for detecting CTCs comprise sample enrichment. CTCs are suitably detected from whole blood using the CellSearch system (Veridex) or a number of alternative methods including staining of enriched or unenriched blood cells with tumor cell specific antibodies or cocktails of antibodies to distinguish the tumor cells from peripheral blood cells.

In some embodiments of the method disclosed herein, a decreased level, relative to a threshold level, of CTCs identifies a patient as a candidate for Bcl-2 family inhibitor therapy. The threshold level can range from about 5-20 CTCs/7.5 mL blood (e.g., 5, 6, 7, 8, 9, 10, 11, 12, 13, 14, 15, 16, 17, 18, 19, or 20 CTCs/7.5 mL). Suitably, the threshold level is about 12 CTC/7.5 mL. A decreased number of CTCs in a sample can be any detectable difference between the sample measurement and the threshold level where the sample level of NSE is less than the threshold (e.g., typically from ~5% to over 100% lower).

4. M30.

The biomarker of the method may be M30. M30 is a caspase cleaved fragment of human keratin 18 protein (or "cytokeratin-18," "CK-18," "keratin-18," "K18") encoded by the KRT18 gene, and is a serum indicator of cellular apoptosis. M30 detects a neoepitope mapped to positions 387 to 396 of a 21-kDa fragment of CK18 (CK18Asp$^{396}$ neoepitope) that is only revealed after caspase cleavage of the protein and is postulated as a selective biomarker of apoptotic cell death. Serum levels of M30 can be measured using any commercially available assay system (Peviva AB, Sweden), and performed using previously described assays that can be validated to good clinical laboratory practice (see, Cummings J., et al., Br J Cancer 92:532-8, 2005; and Cummings J., et al., Br J Cancer 95:42-8, 2006). In some embodiments of the method disclosed herein, an increased level, relative to a threshold level or a baseline level, of M30 identifies a patient as a candidate for Bcl-2 family inhibitor therapy, or that a Bcl-2 family inhibitor therapy is effective. A threshold level can be established by analyzing M30 levels in healthy subjects, or by determining a baseline M30 level prior to therapy. Suitably, an increased level of M30 in a sample can be any detectable difference (typically reported in units per volume) between the sample measurement and the threshold or baseline level where the sample level of M30 is greater than the threshold (e.g., from 1% to over 100% greater).

5. M65.

The biomarker of the method may be M65. M65 is soluble human keratin 18 protein (or "cytokeratin-18," "CK-18," "keratin-18," "K18") encoded by the KRT18 gene, and is a serum indicator of cellular apoptosis. M65 detects a common epitope present in the full-length protein as well as the 21-kDa caspase cleaved fragment and is thus believed to measure, in addition to apoptosis, intact CK18 that is released from cells undergoing necrosis. Like M30, serum levels of M65 can be measured using any commercially available assay system (Peviva AB, Sweden), and performed using previously described assays that can be validated to good clinical laboratory practice (see, Cummings J., et al., Br J Cancer 92:532-8, 2005; and Cummings J., et al., Br J Cancer 95:42-8, 2006). In some embodiments of the method disclosed herein, an increased level, relative to a threshold level or a baseline level, of M65 identifies a patient as a candidate for Bcl-2 family inhibitor therapy, or that a Bcl-2 family inhibitor therapy is effective. A threshold level can be established by analyzing M65 levels in healthy subjects, or by determining a baseline M65 level prior to therapy. Suitably, an increased level of M65 in a sample can be any detectable difference (typically reported in units per volume) between the sample measurement and the threshold or baseline level where the sample level of M65 is greater than the threshold (e.g., from 1% to over 100% greater).

6. Bcl-2/pro-GRP Biomarkers.

The biomarker may be Bcl-2 alone or in combination with pro-GRP. As used herein, Bcl-2 (official symbol BCL2) means the human B-cell CLL/lymphoma 2 gene; Bcl-xl (official symbol BCL2L1) means the human BCL2-like 1 gene; Bcl-w (official symbol BCL2L2) means the human BCL2-like 2 gene. Pro-GRP (official symbol GRP) means the human gastrin releasing peptide.

In some embodiments of the method disclosed herein, an increased level, relative to a threshold level, of pro-GRP identifies a patient as a candidate for Bcl-2 family inhibitor therapy. The threshold level can range from about 500-700 pg/mL (e.g., 500, 510, 520, 530, 540, 550, 560, 570, 580, 590, 600, 610, 620, 630, 640, 650, 660, 670, 680, 690, or 700 pg/mL). Suitably, the threshold level is 600 pg/mL. An increased level of pro-GRP in a sample can be any detectable difference between the sample measurement and the threshold level where the sample level of pro-GRP is greater than the threshold (e.g., from 1% to over 100% greater).

In some embodiments of the method disclosed herein, an amplification of Bcl-2 copy number, relative to a threshold level (normal Bcl-2 copy number), identifies a patient as a candidate for Bcl-2 family inhibitor therapy. The amplification of Bcl-2 copy number, relative to threshold level can range from greater than 2, and in some embodiments include 3 copies to 10 or more copies (e.g., 3, 4, 5, 6, 7, 8, 9, 10, 11, 12, etc.), or 3 copies to 7 copies. Suitably, the amplification of Bcl-2 copy number relative to threshold level is 4 to 5 copies. An increased amplification of Bcl-2 copy number in a sample can be any detectable difference between the sample measurement and the threshold level where the sample level of Bcl-2 copy number is greater than the threshold (e.g., from 10% to over 100% greater).

Bcl-2 and pro-GRP are located at 18q21.1 and 18q21.3, respectively. Chromosomal loci cited herein are based on Build 35 of the Human Genome Map, as accessed through the University of California Santa Cruz Genome Browser. As used herein, reference to a chromosome locus or band, such as 18q21, refers to all of the loci or sub bands, for example, such as 18q21.1 or 18q21.3, within the locus or the band.

As used herein, pro-GRP levels include any of levels of the expressed protein of pro-GRP, of the expressed protein of a pro-GRP precursor, or a fragment of either of the expressed protein of pro-GRP or of a pro-GRP precursor.

7. Other Biomarkers.

The biomarker may be any one or combination of NOXA (official symbol PMAIP1) means the human phorbol-12-myristate-13-acetate-induced protein 1 gene; ABL1 (official symbol ABL1) means the human Abelson murine leukemia viral oncogene homolog 1 gene; RAC1 (official symbol RAC1) means the human ras-related C3 botulinum toxin substrate 1 gene; RASSF3 (official symbol RASSF3) means the human Ras association (RalGDS/AF-6) domain family 3 gene; RAB22A (official symbol RAB22A) means the human member RAS oncogene family gene; BI-1 or BAX inhibitor 1 (official symbol TEGT) means the human testis enhanced gene transcript gene; FAIM-2 (official symbol FAIM) means the human Fas apoptotic inhibitory molecule gene; and RFC2 (official symbol RFC2) means the human replication factor C (activator 1) 2 gene. As used herein, the term "official symbol" refers to EntrezGene database maintained by the United States National Center for Biotechnology Information.

The method detects levels of biomarkers that are useful in classifying a patient as a candidate for Bcl-2 family inhibitor therapy. Accordingly, the biomarker can be any biomolecule that is present and detectable in a patient having cancer, and which can correlate to potential clinical benefit of Bcl-2 family inhibitor therapy. In some embodiments the biomarkers may be Cytokeratin 19 fragment antigen 21-1 (CYFRA 21-1), Neuron-specific enolase (NSE), circulating tumor cells (CTCs), soluble cytokeratin 18 (M65), caspase cleaved fragments of cytokeratin 18 (M30), Bcl-2, or pro-gastrin releasing peptide (pro-GRP), or any combination of two, three, four, five, six, or seven of these biomarkers. In some embodiments the biomarker is CYFRA 21-1, or CYFRA 21-1 in combination with one or more of NSE, CTCs, M65, M30, Bcl-2, or pro-GRP. In some embodiments the biomarker is NSE or NSE in combination with one or more of CYFRA 21-1, CTCs, M65, M30, Bcl-2, or pro-GRP. In some embodiments the biomarker is CTCs or CTCs in combination with one or more of CYFRA 21-1, NSE, M65, M30, Bcl-2, or pro-GRP. In some embodiments the biomarker is M65 or M65 in combination with one or more of CYFRA 21-1, NSE, CTCs, M30, Bcl-2, or pro-GRP. In some embodiments the biomarker is M30 or M30 in combination with one or more of CYFRA 21-1, NSE, CTCs, M65, Bcl-2, or pro-GRP. In some embodiments the biomarker is Bcl-2 or Bcl-2 in combination with one or more of CYFRA 21-1, NSE, CTCs, M65, M30, or pro-GRP. In some embodiments the biomarker is pro-GRP or pro-GRP in combination with one or more of CYFRA 21-1, NSE, CTCs, M65, M30, or Bcl-2.

C) Samples

The method includes collecting samples from a cancer patient for assessment of biomarker levels. The method can use a patient tissue sample of any type or on a derivative thereof, including peripheral blood, serum or plasma fraction from peripheral blood, tumor or suspected tumor tissues (including fresh frozen and fixed or paraffin embedded tissue), cell isolates such as circulating epithelial cells separated or identified in a blood sample, lymph node tissue, bone marrow and fine needle aspirates. The sample suitable for use in the method can comprise any tissue type or cell isolates from any tissue type, including a peripheral blood sample, a tumor tissue or a suspected tumor tissue, a thin layer cytological sample, a fine needle aspirate sample, a bone marrow sample, a lymph node sample, a urine sample, an ascites sample, a lavage sample, an esophageal brushing sample, a bladder or lung wash sample, a spinal fluid sample, a brain fluid sample, a ductal aspirate sample, a nipple discharge sample, a pleural effusion sample, a fresh frozen tissue sample, a paraffin embedded tissue sample or an extract or processed sample produced from any of a peripheral blood sample, a serum or plasma fraction of a peripheral blood sample, a tumor tissue or a suspected tumor tissue, a thin layer cytological sample, a fine needle aspirate sample, a bone marrow sample, a lymph node sample, a urine sample, an ascites sample, a lavage sample, an esophageal brushing sample, a bladder or lung wash sample, a spinal fluid sample, a brain fluid sample, a ductal aspirate sample, a nipple discharge sample, a pleural effusion sample, a fresh frozen tissue sample or a paraffin embedded tissue sample. For example, a patient peripheral blood sample can be initially processed to extract an epithelial cell population, a plasma fraction or a serum fraction, and this extract, plasma fraction or serum fraction can then be assayed. A microdissection of the tissue sample to obtain a cellular sample enriched with suspected tumor cells can also be used. The preferred tissue samples for use herein are peripheral blood and serum fractions thereof.

The tissue sample can be processed by any desirable method for performing protein-based assays. For in situ hybridization assays potentially used with the inventive assays to confirm the presence of biomarker copy number gain, a paraffin embedded tumor tissue sample or bone marrow sample is fixed on a glass microscope slide and deparaffinized with a solvent, typically xylene. Useful protocols for tissue deparaffinization and in situ hybridization are available from Abbott Molecular Inc. (Des Plaines, Ill.). Any suitable instrumentation or automation can be used in the performance of the inventive assays. PCR based assays can be performed on the m2000 instrument system (Abbott Molecular, Des Plaines, Ill.). Automated imaging can be employed for the preferred fluorescence in situ hybridization assays.

The sample may comprise a peripheral blood sample from a patient which is processed to produce an extract of circulating tumor cells having increased chromosomal copy number of at least one biomarker. The circulating tumor cells can be separated by immunomagnetic separation technology such as that available from Immunicon (Huntingdon Valley, Pa.) or by a variety of other enrichment and selection methods. The number of circulating tumor cells showing at least one copy number gain is then compared to the baseline level of circulating tumor cells having increased copy number determined preferably at the start of therapy. Increases in the number of such circulating tumor cells can indicate therapy failure.

Test samples for assays to confirm copy number gain or deletion can comprise any number of cells that is sufficient for a clinical diagnosis, and typically contain at least about 8-100 cells. In a typical FISH assay, the hybridization pattern is assessed in about 25-1,000 cells. Test samples are typically considered "test positive" when found to contain the chromosomal gain or deletion in a sufficient proportion of the sample. The number of cells identified with chromosomal copy number and used to classify a particular sample as positive, in general will vary with the number of cells in the sample. The number of cells used for a positive classification is also known as the cut-off value. Examples of cutoff values that can be used in the determinations include about 5, 25, 50, 100 and 250 cells, or 5%, 10%, 15%, 20%, 25%, 30%, 35%, 40%, 50% and 60% of cells in the sample population. As low as one cell may be sufficient to classify a sample as positive, relative to a threshold value. In a typical paraffin embedded tissue sample, it is preferred to identify at least 30 cells as positive and more preferred to identify at least 20 cells as positive for having the chromosomal copy number gain or deletion. For example, detection in a typical paraffin embedded small cell lung cancer tissue of 30 cells having gain or deletion of a biomarker would be sufficient to classify the tissue as positive and eligible for treatment with a Bcl-2 family inhibitor.

II) Method for Determining Chromosome Number

Aspects of the disclosure are further directed to a method for assessing in a patient tissue sample, the chromosome copy number change at chromosome locus 18q21-q22, preferably at either chromosome band 18q21-q22 or band 14q11, and more preferably at both 18q21-q22 and 14q11. Chromosome region 18q21-q22 encompasses the chromosomal DNA sequence of the Bcl-2 gene and the pro-GRP gene at 18q21.3 and the NOXA gene at 18q21.32. Chromosome region 14q11 encompasses the chromosomal DNA sequence of the Bcl-w gene at 14q11.2. It is also within the invention to assess the chromosomal locus of the Bcl-XL gene at 20q11.2. Suitably, however, assessment of the 18q21-q22 and 14q11 discriminant regions is performed as gains of these loci were correlated to SCLC sensitivity to ABT-737, whereas gain of 20q11.2 showed no correlation to ABT-737 sensitivity.

These genomic biomarkers were identified through comparative genomic hybridization (CGH) analysis of 23 SCLC cell lines used to test Bcl-2 inhibitors in vitro and in vivo and investigation of their clinical significance. These genomic biomarkers are of particular interest for use in companion diagnostic assays to the use of ABT-737 Bcl-2 inhibitor therapy against SCLC and lymphoma. Although Zhao, X., et al., "Homozygous deletions and chromosome amplifications in human lung carcinomas revealed by single nucleotide polymorphism array analysis", Cancer Res., 65: 5561-5570, 2005 (hereafter referred to as Zhao et al.), reports on the genome-wide analysis of 5 SCLC cell lines and 19 SCLC patient tumors using 100K SNP genotyping microarrays, Zhao et al. do not disclose chromosome copy number gain at 18q21-q22 nor at 14q11.

The disclosure identifies multiple other novel regions of chromosome copy number change not previously reported in SCLC. These other novel genomic biomarkers are listed in Table 1 below and are also not reported in Zhao et al. A gain of the locus of ABL1 at 9q34 can be potentially used to identify patients for treatment with the ABL1 kinase inhibitor imatinib mesylate, Gleevec® (Gleevec is a registered trademark of Novartis). Copy number gains at three members of the Ras family, RAC1 at 7p22.1 (gains in 69% of lines and 66% of 19 tumors studied), RASSF3 at 12q24 (65% of lines and 70% of 19 tumors studied), and RAB22A at 20q13.3 (42% of lines and 84% of 19 tumors studied), are notable because of the known oncogenic impact of Ras family genes and the high percentage occurrence in the tumor cohort studied. Gains at other anti-apoptotic genes were seen for BI-1 at 12q12-q14, FAIM-2 (gained in 73% of lines and 58% of 19 tumors studied) at 12q13.12, and RFC2 (gained in 71% of lines and 60% of 19 tumors studied) at 7q11. Diagnostic assays for detecting any of these copy number changes in small cell lung cancer or other cancer is another embodiment of the invention.

A bioinformatics approach identified regions of chromosomal aberrations that discriminate between cell line groups that were sensitive and resistant to ABT-737. This approach tested for statistical significance using Fisher's Exact Test to determine if a SNP identified through the CGH analysis shows preferential gain/loss in the sensitive or resistant group. The copy number thresholds for amplifications and deletions used in this analysis were set at 2.8 and 1.5, respectively. Contiguous regions of probesets (SNPs) with low table and two-sided p-values were then subjected to further analysis. One large region on chromosome 18q was of particular interest because of high copy numbers and low p-values. This region spans chromosomal bands 18q21.1 through 18q22. Real-time qPCR was used to validate this region as a potential therapy stratification marker. qPCR was used to evaluate six loci starting at 48 Mb (18q21.1) and ending at 62 Mb (18q22) within chromosome 18. The qPCR results are displayed in FIG. 1 and show segregation between the sensitive and resistant lines based on the copy number of the test locus (ANOVA test p-value <0.0001). The sensitive lines carry an amplification of the region under consideration (3 to 7 copies), whereas the resistant lines display a normal copy number. The target of ABT-737, Bcl-2, is located within this discriminant region and had a low 0.04 p-value for significance in determining sensitivity. An analysis of a 62 patient SCLC cohort for copy number gains at 18q21-q22 was performed and found copy number gain in 48% of this cohort, with low-level amplifications of the Bcl-2 gene present in 40% of the patients (25 out of 62) and high-level amplifications in 8% of the tumors (5 out of 62).

Assessment of copy number gain at the 18q21-q22 and 14q11 discriminant regions are believed applicable for patient classification for other cancer chemotherapy, such as treatment with cytotoxic drugs, DNA-damaging drugs, tubulin inhibitors, tyrosine kinase inhibitors, and anti-metabolites. The Bcl-2 genes provide significant cell survival benefit, and their chromosome copy number gain driving their expression is expected to mark therapy resistance.

III) Kits

In another aspect, the disclosure provides kits for the measurement of biomarker levels that comprise containers containing at least one labeled probe, protein, or antibody specific for binding to at least one of the expressed biomarkers in a sample. These kits may also include containers with other associated reagents for the assay. In some embodiments, a kit comprises containers containing a labeled monoclonal antibody or nucleic acid probe for binding to a biomarker and at least one calibrator composition. The kit can further comprise components necessary for detecting the detectable label (e.g., an enzyme or a substrate). The kit can also contain a control sample or a series of control samples which can be assayed and compared to the test sample. Each component of the kit can be enclosed within an individual container and all of the various containers can be within a single package, along with instructions for interpreting the results of the assays performed using the kit.

EXAMPLES

Example 1

A whole-genome screen with high-density SNP genotyping arrays identified recurrent gene amplifications/deletions in SCLC cells. Recurrent chromosomal copy number gains were identified, were confirmed by real-time qPCR, and were then validated as present in an independent SNP analysis dataset of 19 SCLC tumors obtained from Zhao et al. One of these copy number gains, on 18q, was correlated with sensitivity of SCLC cell lines to the targeted cancer drug ABT-737. The clinical relevance of the 18q21 gain was then verified by FISH analysis of SCLC tumors. The genes residing in the 18q21 marker region were shown to be overexpressed in the sensitive cell lines.

Materials and Methods

Cell Culture.

The following SCLC cell lines were obtained from ATCC (Manassis, Va.): NCI-H889, NCI-H1963, NCI-H1417, NCI-H146, NCI-H187, DMS53, NCI-H510, NCI-H1209, NCI-H526, NCI-H211, NCI-H345, NCI-H524, NCI-H69, NCI-H748, DMS79, NCI-H711, SHP77, NCI-446, NCI-H1048, NCI-H82, NCI-H196, SW1271, H69AR. All cells were cultured in the ATCC recommended media at 37° C. in a humidified atmosphere containing 5% $CO_2$. Genomic DNA was isolated from the cell lines using a DNAeasy kit (Qiagen, Valencia, Calif.). Comparative Genomic Hybridization.

Genomic DNA from the SCLC cell lines was run on 100K SNP genotyping array sets (Affymetrix, Santa Clara, Calif.). Each 100K set consists of two 50K arrays, HindIII and XbaI. Briefly, 250 ng of genomic DNA from each cell line was digested with the corresponding restriction enzyme (HindIII or XbaI, New England Biolabs, Boston, Mass.). Adapters were ligated to the digested DNA, followed by PCR amplification with Pfx DNA polymerase (Invitrogen, Carlsbad, Calif.). The PCR products were purified, fragmented, labeled, and hybridized to the SNP microarray according to the manufacturer's protocol. After a 16-hour hybridization, the arrays were scanned, and the data were processed using the Affymetrix GTYPE software to create copy number (.cnt) files containing information on the inferred copy number for each probeset (SNP). The GTYPE software generates an inferred copy number for each SNP by comparing the signal intensity for the sample with an internal data set from a healthy population, which is included in the GTYPE software. The .cnt files contained combined information from both arrays in the set. These files were converted into .txt files and loaded into an internally developed software program for further analysis.

A program was used for the graphical display and analysis of multiple .txt files. The data were displayed chromosome by chromosome as a histogram of copy number versus SNP's ordered sequentially along the chromosome. For each SNP, the predicted cytogenetic band as well as any genes between this and the next adjacent SNP were reported. The gene coordinates and cytogenetic band positions were inferred from the Build 35 of the Human Genome. From a selected region of the histogram, for example, 18q21, a summary file can be produced that contains the coordinates of all probesets on the microarray for that region (individual SNP's) with the corresponding copy numbers, cytogenetic bands, gene IDs, names, and the coordinates of all the genes residing in the region (regardless of whether a gene is actually represented by SNP's on the array). In the analysis, contiguous SNP's with a small p-value (p-value <0.08) were considered to be one region.

To facilitate identification of recurrent aberrations, the frequency of copy number change was calculated and plotted for each probeset (SNP) on the microarray, using a threshold of ≥2.8 copies for copy number gains and of ≤1.5 copies for copy number losses. The cell lines were then classified as sensitive and resistant to ABT-737. Fisher's Exact Test was used to identify aberrations in the copy number data that were associated with the sensitivity of cell lines to the Bcl-2 inhibitor. For each SNP, a 2×2 contingency table was constructed for testing the significance of an increase or decrease in copy number in the two groups.

Raw microarray hybridization data produced in a study of SCLC by Zhao et al. (incorporated herein by reference), and analyzed for copy number aberrations, identified them, and compared these copy number changes to those identified in the study of the SCLC cell lines below.

Real-Time Quantitative PCR (qPCR).

Primers were designed using the Vector NTI software (Invitrogen) and tested to ensure amplification of single discrete bands with no primer dimers. All primers were synthesized by IDT (Coraville, Iowa). Two independent forward and reverse primer pairs were used for each of the six loci within the 18q21-q22 discriminant region. The primer sequences used are listed in pairs with each pair's approximate location from the 18p terminus, with the forward primers having odd Sequence Identification Numbers (SEQ ID NO's) and the reverse primers having even SEQ ID NO's, and were:

| From 18p | Sequence | SEQ ID NO |
|---|---|---|
| 48MB | TCCTGAGGGTCTTCTCTGTGGAGG | (SEQ ID NO: 1) |
| 48MB | TGTGCCTGGAATACATCTCCGAGA | (SEQ ID NO: 2) |
| 48MB | TAAGACAGATCACCTTCCAAGAGAGACAC | (SEQ ID NO: 3) |
| 48MB | CACAGGCTGCACTTTAGAGGCAA | (SEQ ID NO: 4) |
| 53MB | CAACAGCATGTGCTTCATAGTTGCC | (SEQ ID NO: 5) |
| 53MB | CGACAGCACTGCCCACTCTAGTAATAG | (SEQ ID NO: 6) |
| 53MB | AACAAACACTTGAAGACACTGAAGAACAAC | (SEQ ID NO: 7) |
| 53MB | TGCTCTCAACTGAAAATGGCTATATGTC | (SEQ ID NO: 8) |
| 54MB | TCTTCCAGGGCACCTTACTGTCC | (SEQ ID NO: 9) |
| 54MB | ACCAGCAACCCCATTCCGAG | (SEQ ID NO: 10) |
| 54MB | TTGATGTGTCCCCTGTGCCTTTA | (SEQ ID NO: 11) |
| 54MB | ACAAGTTTTTGCCTCTAGATGACACTGTT | (SEQ ID NO: 12) |
| 55MB | AACCCGAGGAAGTCTAAATGAATAAT | (SEQ ID NO: 13) |
| 55MB | CACACCCAGTTACCCCTGTTATTAAC | (SEQ ID NO: 14) |
| 55MB | TCCTCTCTCATCTGTAGTCTGGCTTTA | (SEQ ID NO: 15) |
| 55MB | AAACTATAATAGCAATCTGTGCCCAA | (SEQ ID NO: 16) |
| 59MB | AGCATTGGTGCGTGTGGTGC | (SEQ ID NO: 17) |
| 59MB | CCTCTTGGTGGAATCTAGGATCAGG | (SEQ ID NO: 18) |
| 59MB | TTCAAGTGAAGTTACCTAATGCTCCC | (SEQ ID NO: 19) |
| 59MB | CCTGGGGTACAGAAATACTTAGTGAT | (SEQ ID NO: 20) |
| 62MB | TTGGAAAGTCTGGATGGGAATCTTTT | (SEQ ID NO: 21) |
| 62MB | AGGGGATTTAACCTACCTTTGTTTC | (SEQ ID NO: 22) |
| 62MB | ATGACAATTAAATTATCACGCTTCCA | (SEQ ID NO: 23) |
| 62MB | TTCTTCTTGTCAGCAGCCACTTATCA | (SEQ ID NO: 24) |

Real-time, quantitative PCR was conducted on an iCycler thermocycler (Bio-Rad, Hercules, Calif.) using SYBR Green qPCR supermix UDG (Invitrogen). Each reaction was run in triplicate and contained 10 ng of purified genomic DNA along with 300 nM of each primer in a final volume of 50 μl. The cycling parameters used were: 95° C. for 3 min.; 35 cycles of 95° C. for 10 sec.; 57° C. for 45 sec. Melting curves were performed to ensure that only a single amplicon was produced and samples were run on a 4% agarose gel (Invitrogen) to confirm specificity. Data analysis was performed in the linear regression software DART-PCR v1.0, see Peirson, S, N., et al., "Experimental validation of novel and conventional approaches to quantitative real-time PCR data analysis", Nucleic Acids Res., 31: e73, 2003, using raw thermocycler values. Normalization of sample input was conducted using geometric averaging software GeNorm v3.3 to GAPDH, β-2 microglobulin, YWHAZ, RPL13a, and PLP-1, see Vandesompele, J, De Preter K et. al., "Accurate normalization of real-time quantitative RT-PCR data by geometric averaging of multiple internal control genes", Genome Biol., 2002 Jun. 18; 3 (7):RESEARCH0034, Epub 2002 Jun. 18, PMID 12184808 [PubMed—indexed for MEDLINE]. The copy number for each locus evaluated was determined by establishing the normalized qPCR output for the sample and dividing this value by the normalized qPCR output of a control genomic DNA (Clontech, Mountain View, Calif.) and multiplying this value by two. Each qPCR copy number estimate is the average value for two independent primer sets (mean CV 11.5%).

Fluorescent In Situ Hybridization.

A tissue microarray containing primary SCLC tumors from 62 patients provided by Dr. Guido Sauter of the Department of Pathology, University Medical Center, Hamburg-Eppendorf, was analyzed by FISH using a commercially available dual-color FISH probe targeting 18q21 (LSI Bcl-2 Break-apart probe, Abbott Molecular). This LSI Bcl-2 FISH probe contains two probes labeled in different fluorescent colors that hybridize adjacent to each side of the Bcl-2 locus at 18q21.3, but does not hybridize to any of the genomic sequence of Bcl-2. The slides were deparaffinized for 10 minutes in Xylol, rinsed in 95% EtOH, air-dried, incubated in a Pretreatment Solution (Abbott Molecular) for 15 minutes at 80° C., rinsed in water, incubated in a Protease Buffer (Abbott Molecular) for 2.5 to 5 hours, rinsed in water, dehydrated for 3 min each in 70, 80, and 95% EtOH, and air-dried. 10 µl of the probe mix was applied onto the slide, and the slide was covered, sealed, heated to 72° C. for 5 minutes, and hybridized overnight at 37° C. in a wet chamber. The slides were then washed with a wash buffer containing 2×SSC and 0.3% NP40 (pH 7-7.5) for 2 minutes at 75° C., rinsed in water at room temperature, air-dried, mounted with a DAPI solution and a 24×50 mm coverslip, and examined under an epifluorescence microscope. For each tissue sample, the range of red and green FISH signals corresponding to the Bcl-2 locus was recorded. An average copy number per spot was then calculated based on the minimal and maximal number of FISH signals per cell nucleus in each tissue spot. Copy number groups were then built according to the following criteria:

(1) 1-2 signals=average copy number <2.5;
(2) 3-4 signals=average copy number <4.5;
(3) 5-6 signals=average copy number <6.5; and
(4) 7-10 signals=average copy number >6.5.

Microarray Analysis of Gene Expression.

Total RNA was isolated by using the Trizol reagent (Invitrogen,) and purified on RNeasy columns (Qiagen, Valencia, Calif.). Labeled cRNA was prepared according to the microarray manufacturer's protocol and hybridized to human U133A 2.0 arrays (Affymetrix, Santa Clara, Calif.). The U133A 2.0 chips contain 14,500 well-characterized genes, as well as several thousand ESTs. The microarray data files were loaded into the Rosetta RESOLVER™ software for analysis and the intensity values for all probesets were normalized using the Resolver's Experimental Definition. The intensity values for the probesets corresponding to genes within the amplified regions were normalized across each gene and compared in heatmaps using the SPOTFIRE™ software.

Results

Table 1 summarizes all copy number abnormalities that were identified as (i) present in ≥40% of the tested cell lines, and (ii) present in ≥40% of the 19 SCLC tumors from the reviewed raw hybridization dataset, and (iii) as not previously reported in the literature. The list of identified novel aberrations includes gains of 2q, 6p, 7p, 9q, 11p, 11q, 12p, 12q, 13q, 14q, 17q, 18q, 20p, 20q, 21q, and 22q and losses of 110q21.1. All of these were confirmed by real-time qPCR in selected cell lines. As can be seen in Table 1, all of these identified novel aberrations are relatively short (about 70 kb to about 3.6 Mb). The mean spacing between the SNPs on the 100K SNP array used in this study is 23.6 kb, thus permitting identification of very short regions of gains and losses. It is possible that some of the newly detected recurrent copy number changes represent copy number polymorphisms, as opposed to disease driven changes. However, this is only a remote possibility, because the copy number was determined relative to a panel of 110 normal individuals, see Huang, J., et al., "Whole genome DNA copy number changes identified by high density oligonucleotide arrays", Hum. Genomics, 1: 287-299, 2004.

TABLE 1

| Copy Number Abnormality | Length | Frequency in cell lines | Frequency in tumors | Genes in this locus with reported association with cancer |
|---|---|---|---|---|
| Gain of 2q37.1-q37.2 | 420 kb | 61% | 66% | |
| Gain of 6p21.31 | 3.63 Mb | 69% | 63% | CK2B, MSH5 |
| Gain of 7p22.1 | 270 kb | 69% | 54% | RAC1 |
| Gain of 7p14.3 | 40 kb | 75% | 41% | |
| Gain of 7q11.21 | 560 kb | 47% | 42% | |
| Gain of 7q22.1 | 2.51 Mb | 71% | 60% | RFC2, FZD9, BCL7B |
| Gain of 7q36 | 190 kb | 55% | 80% | PTPRN2 |
| Gain of 9q34.1 | 130 kb | 72% | 54% | ABL1 |
| Gain of 9q34.2 | 1.86 Mb | 58% | 63% | |
| Loss of 10q21.1 | 480 kb | 85% | 98% | |
| Loss of 10q21.1 | 340 kb | 53% | 42% | |
| Loss of 11p11.12 | 189 Mb | 57% | 44% | |
| Gain of 11q13.2-q13.3 | 230 kb | 41% | 46% | |
| Gain of 11q13.4 | 390 kb | 59% | 60% | |
| Gain of 11q23.3 | 390 kb | 88% | 81% | |
| Gain of 12p13 | 430 kb | 74% | 41% | DDX6, BCL9L, FOXR1, TMEM24 |
| Gain of 12p13.31 | 48 kb | 52% | 96% | |
| Gain of 12q13.12 | 490 kb | 57% | 83% | TNFRSF1A, CHD4 |
| Gain of 12q14.2 | 340 kb | 73% | 58% | BAX inhibitor-1, FAIM-2 |
| Gain of 12q24.11 | 98 kb | 65% | 70% | RASSF3 |
| Gain of 12q24.12 | 260 kb | 80% | 67% | |
| Gain of 12q24.13 | 180 kb | 86% | 46% | |
| Gain of 12q24.33 | 10 kb | 61% | 58% | |
| Gain of 13q34 | 750 kb | 55% | 85% | MMP17 |
| Gain of 14q11 | 130 kb | 43% | 47% | |
| Gain of 14q23.2 | 70 kb | 48% | 40% | ER2 |
| Gain of 14q24.3 | 410 kb | 46% | 45% | |
| Gain of 14q24.3 | 1.05 Mb | 54% | 47% | |
| Gain of 14q24.3-q31 | 160 kb | 51% | 52% | CHES1 |
| Gain of 14q32.12 | 2.36 Mb | 50% | 56% | |
| Gain of 14q32.1-32.2 | 6 Mb | 48% | 61% | TCL6 |
| Gain of 14q32.33 | 1.84 Mb | 83% | 78% | TMEM121 |
| Gain of 17q21.33 | 230 kb | 43% | 70% | |
| Gain of 17q24.3-q25.1 | 2.62 Mb | 53% | 77% | |
| Gain of 17q25.3 | 1.12 Mb | 59% | 61% | |
| Gain of 18q12 | 190 kb | 46% | 54% | |
| Gain of 18q21.1 | 370 kb | 48% | 51% | |
| Gain of 18q22-q23 | 400 kb | 46% | 88% | |
| Gain of 20p13 | 370 kb | 57% | 45% | |
| Gain of 20p13-p12 | 190 kb | 59% | 49% | |
| Gain of 20p11.23 | 300 kb | 62% | 41% | |
| Gain of 20p11.21 | 790 kb | 52% | 40% | |
| Gain of 20q11.21 | 230 kb | 64% | 98% | |
| Gain of 20q11.23 | 280 kb | 35% | 56% | |

TABLE 1-continued

| Copy Number Abnormality | Length | Frequency in cell lines | Frequency in tumors | Genes in this locus with reported association with cancer |
|---|---|---|---|---|
| Gain of 20q12-q13.1 | 190 kb | 43% | 98% | |
| Gain of 20q13.1-q13.13 | 2.45 Mb | 60% | 58% | PREX1, CSE1L |
| Gain of 20q13.32-13.33 | 40 kb | 42% | 84% | RAB22A |
| Gain of 20q13.3 | 2.74 Mb | 47% | 57% | |
| Gain of 21q22.3 | 1.47 Mb | 57% | 69% | |
| Gain of 22q13.1 | 66 kb | 65% | 61% | |

The 23 SCLC cell lines were tested for sensitivity to ABT-737 using the procedure described in Oltersdorf, T., "An inhibitor of Bcl-2 family proteins induces regression of solid tumours", Nature, 435: 677-681, 2005, with a cell line classified as sensitive if its EC50 <1 μM and as resistant if its $EC_{50}$>10 μM. The sensitive cell line group consisted of NCI-H889, NCI-H1963, NCI-H1417, NCI-H146, NCI-H187, DMS 53, NCI-H510, NCI-H209, NCI-H526, NCI-H211, NCI-H345, and NCI-H524 and the resistant cell line group was comprised of NCI-H82, NCI-H196, SW1271, and H69AR.

To identify potential genomic correlates of the sensitivity of SCLC cells to ABT-737, we developed a bioinformatics approach that identifies regions of chromosomal aberrations that discriminate between the sensitive and resistant groups. Our program tested for statistical significance using Fisher's Exact Test to determine if a SNP shows preferential gain/loss in the sensitive or resistant group. The copy number thresholds for amplifications and deletions were set at 2.8 and 1.5, respectively. Contiguous regions of probesets (SNPs) with low table and two-sided p-values were subjected to further analysis. The top discriminating aberration represents a long region of chromosome 18, starting at nucleotide position 45704096 and ending at nucleotide position 74199087 and spanning the chromosomal bands 18q21.1 through 18q22.1 (nucleotide positions are from Build 35 of the Human Genome Map).

Real-time qPCR was then applied to validate the 18q21 region identified in the copy number analysis as a potential stratification marker. Two different primer sets run in triplicate were used to evaluate six loci starting at 48 Mb from the chromosome 18p terminus (18q21.1) and ending at 62 Mb from the chromosome 18p terminus (18q22). The qPCR results are shown in FIG. 1, with the copy number measured at each locus plotted against sensitivity to ABT-737. FIG. 1 shows segregation between the sensitive and resistant lines based on the copy number of the test locus (ANOVA test p-value <0.0001), thus confirming the copy number analysis. The sensitive lines carry an amplification of the region under consideration (3 to 7 copies), whereas the resistant lines display a normal copy number. Further, the most sensitive lines (H889, H1963, H1417, and H146) have the highest Bcl-2 copy number (4 or 5 copies).

Figure 2:
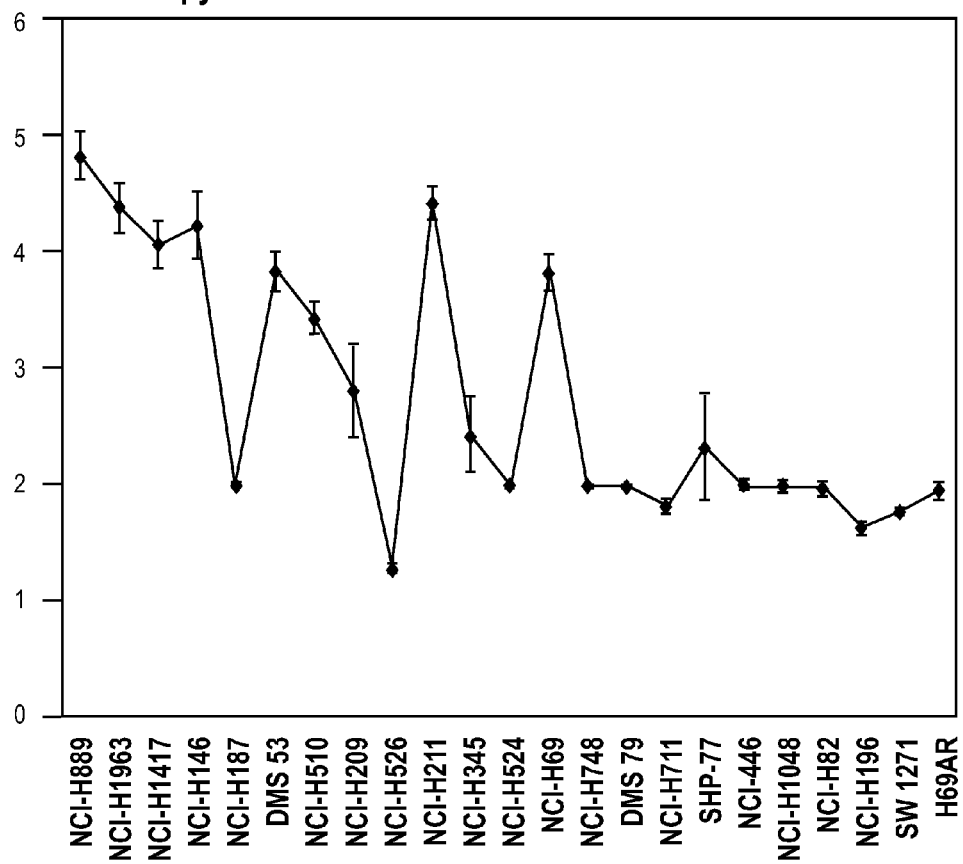
FIG. 2 depicts the relationship between the Bcl-2 gene copy number of SCLC cell lines and sensitivity of the cell lines to ABT-737.

Notably, the Bcl-2 gene (p-value 0.04), the target of ABT-737, is located within the 18q21-q22 discriminant region at 18q21.3, which led to investigation of whether the sensitivity of a cell line to the drug may be determined by the amplification status of the Bcl-2 gene. FIG. 2 illustrates the relationship between the Bcl-2 gene copy number and the sensitivity of the SCLC cell lines. The cell lines are arranged from left to right in the order of decreasing sensitivity to the drug, as determined by the $EC_{50}$ values for the cell lines from Oltersdorf, T., et al., "An inhibitor of Bcl-2 family proteins induces regression of solid tumours", Nature, 435: 677-681, 2005.

The copy number for each cell line in FIG. 2 is the average of the copy numbers for 17 SNP's within the Bcl-2 gene measured by the 100K mapping array set. The copy number for the NOXA and Bcl-w genes was the number determined for at least three contiguous SNP's surrounding their gene loci. It is clear from the plot that the sensitivity of the SCLC cell lines correlates with the Bcl-2 copy number. The most sensitive lines (H889, H1963, H1417, and H146) have the highest Bcl-2 copy number (4 or 5 copies). Another apoptosis-related gene (NOXA), whose product promotes degradation of Mc1-1, is located next to Bcl-2 and has a similar copy number profile. There are two outliers in this dataset, which are sensitive, but have a normal copy number of the Bcl-2 gene (H187 and H526). However, both H187 and H526 cell lines have copy number gain of the Bcl-w gene at 14q11.2, which is also a target of the drug. Their sensitivity to ABT-737 is attributed to the extra copy of the Bcl-w gene at 14q11.2. A similar plot did not show any correlation of sensitivity to Bcl-XL copy number gain, although copy number gain was seen in some cell lines. Thus, a correlation was established between the amplification of Bcl-2 and NOXA on 18q21.3 and the sensitivity of SCLC cell lines to ABT-737. This observation is consistent with the mechanism of action of the drug and suggests that the single-agent sensitivity of a cell line to the drug may be determined by the copy number status of 18q21, particularly the 18q21.3 locus of Bcl-2 and NOXA.

The relative expression of the 18q genes in the ABT-737 sensitive and resistant SCLC cell lines was profiled with expression microarrays as described above. The 12 most sensitive cell lines and four resistant lines were analyzed for expression of all genes located on the discriminant region on 18q21-q22 and present on the Affymetrix U133A microarray used. The genes in the amplified region were found overexpressed in the sensitive lines relative to the resistant ones. Overall, the finding of overexpression of the 18q21-q22 genes implies a significant degree of correlation between gene amplification and gene overexpression. These data further support for the selection of the 18q21-q22 copy number gain as a patient stratification biomarker in SCLC.

Figure 3:
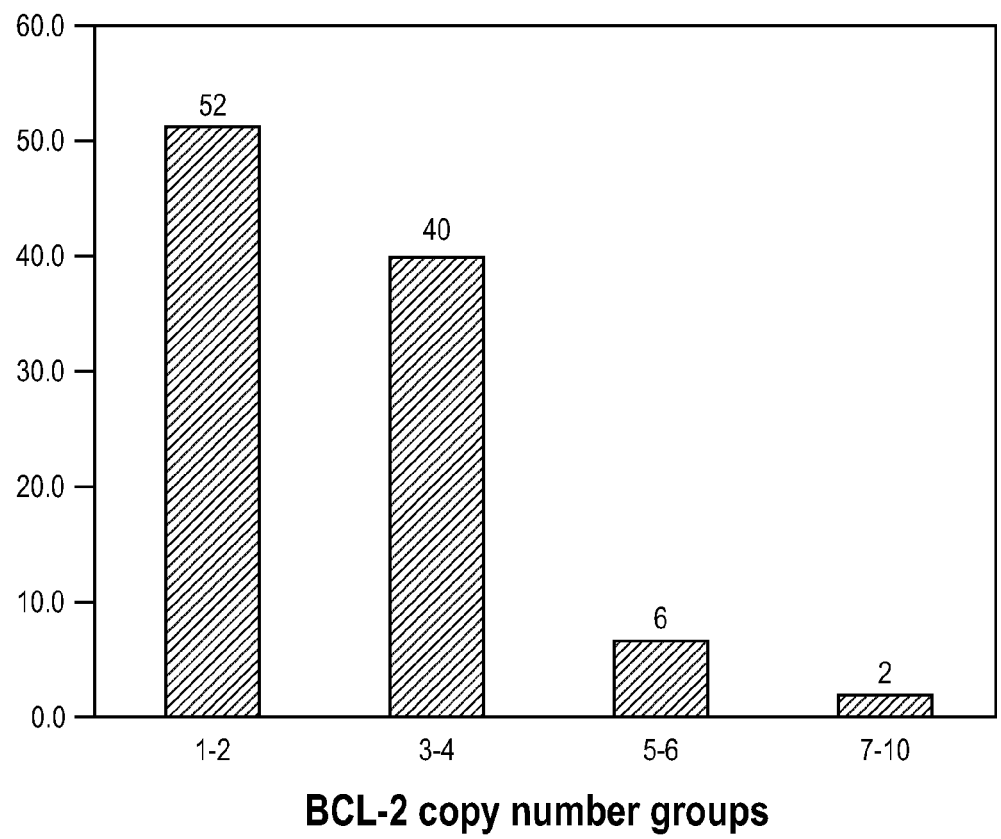
FIG. 3 shows classification of a 62 patient cohort of clinical SCLC samples by chromosome copy number of the Bcl-2 locus.

To determine the clinical relevance of the 18q21-q22 marker, the Bcl-2 copy number in SCLC tumors using FISH with a commercially available Bcl-2 locus probe set. Although the commercial FISH probe used did not contain any of the Bcl-2 gene sequence itself, the probe used contain sequences that hybridize on both sides of the gene, and a continguous copy number increase seen with both parts of this probe included a gain of the Bcl-2 locus also. The analysis included SCLC tumors from 62 patients arrayed on a tissue microarray. The data is shown in FIG. 3. Copy number gains were seen in 48% of the cohort, with low-level amplifications of the Bcl-2 gene present in 40% of the patients (25 out of 62) and high-level amplifications in 8% of the tumors (5 out of 62). This finding is consistent with the copy number data from the SCLC cell lines, as most copy number changes in the cell lines were also low-level gains. The percentage of lines carrying the aberration was also similar (40%).

Example 2

The following Example 2 describes determination of levels of pro-GRP in four cell lines showing elevated copy number for the Bcl-2 locus. The cell lines tested were NCI-H889, NCI-H146, DMS53 and NCI-H510, and these cell lines had shown sensitivity to the Bcl-2 inhibitor. The cells from each were cultured for seven days at 37° C., then the medium was collected and stored at −70° C. for one week. The medium from each cell line was thawed on ice, and then tested by a commercially available ELISA assay (distributed by IBL and made by Advanced Life Sciences Institute, Japan) for pro-GRP levels. The pro-GRP levels were estimated for the DMS53 cell line because the OD was outside the top range of the standard curve for the assay. The pro-GRP levels in picograms pro-GRP per milliliter per micrograms of total protein (pg pro-GRP/ml/µg protein) were:

| | |
|---|---|
| NCI-H889 | about 2.9 |
| NCI-H146 | about 0.1 |
| DMS53 | about 9.5 |
| NCI-H510 | about 2.0 |

Higher levels of pro-GRP correlating to the presence of the chromosomal copy number increase were seen in the NCI-H889, DMS53 and NCI-510 cell lines.

Example 3

This example illustrates a phase I dose-escalation study to evaluate the safety, pharmacokinetics, and preliminary efficacy of navitoclax in subjects with relapsed or refractory SCLC and other solid tumors. This phase I study of navitoclax, a novel inhibitor of Bcl-2 family proteins, was designed to evaluate safety, pharmacokinetics, and preliminary efficacy in subjects with small cell lung cancer (SCLC) or other solid tumors.

As this study is of a targeted therapy against Bcl-2 interactions, it also provided the opportunity to evaluate potential biomarkers of response. It was recently demonstrated that amplification of a region of 18q that contains Bcl-2 correlates with SCLC cell line sensitivity in vitro to ABT-737 (Olejniczak E T, Van Sant C, Anderson M G, et al: Integrative genomic analysis of small-cell lung carcinoma reveals correlates of sensitivity to bcl-2 antagonists and uncovers novel chromosomal gains. Mol Cancer Res 5:331-9, 2007). Evaluation of this region in 62 SCLC tumor samples confirmed amplification at low-levels in 40% and high-levels in 8%, consistent with prior reports of Bcl-2 overexpression in SCLC. Notably, this region contains not only Bcl-2, but the gene for another potential marker of SCLC, pro-gastrin releasing peptide (pro-GRP). Pro-GRP is a peptide secreted from SCLC cells that has been studied for years as a potential biomarker of disease progression and response to therapy in SCLC. In the context of this phase I study, we also evaluated levels of circulating pro-GRP in addition to circulating tumor cells and markers of epithelial cell apoptosis.

Methods

Subjects enrolled to intermittent dosing cohorts received navitoclax on Days 1-14 followed by 7 days off. Subjects on continuous dosing cohorts received a one week lead-in dose of 150 mg followed by continuous daily administration of navitoclax. Blood samples were collected for pharmacokinetic analyses, biomarker analyses, and platelet monitoring.

Eligibility.

Subjects included histologically documented SCLC or other non-hematologic malignancies, age ≥18, Eastern Cooperative Oncology Group performance status (ECOG PS) of ≤2, measurable disease by Response Evaluation Criteria in Solid Tumors (RECIST 1.0), and had received at least one prior chemotherapy treatment with documented progression. Subjects with brain metastases were included if they had surgery and/or radiation therapy followed by 21 days of stable neurologic function and stable disease by imaging prior to the first dose of study drug. Additional inclusion criteria included adequate bone marrow, renal and hepatic function per local laboratory reference range, non-pregnant status, and a life expectancy of ≥90 days.

Subjects were excluded if they had an underlying predisposing condition to or active bleeding, recent history of thrombocytopenia-associated bleeding, active immune thrombocytopenic purpura, autoimmune hemolytic anemia, or peptic ulcer disease, refractoriness to platelet transfusions within one year, need for full-dose anticoagulation, steroid or aspirin therapy within 7 days.

The clinical trial protocol was approved and monitored by all local institutional review boards and all patients provided written informed consent.

Biomarker Assessment.

Blood samples for circulating tumor cells (CTCs) were collected at screening, C1D14, C2D14, and at the end of study treatment. Samples for the plasma marker Pro-GRP were collected at screening, C1D14, C2D14, and at the end of study. Samples for serum marker M30 were collected at screening, pre-dose, 6 and 24 hours post-dose on C1D-3 (for 14/21 day dosing) or lead-in day 2 for 21/21 day dosing). Samples were also collected on C1D14; pre-dose and 6 hours post-dose on C2D1; C2D14; end of cycle 4; and every $3^{rd}$ cycle thereafter and at the final visit for all subjects.

The CTC were analyzed via the CellSearch system (Veridex, Raritan, N.J.). Blood (10 mL) was collected in CellSearch tubes and processed within a maximum of 72 hours after collection. Fluorescence in-situ hybridization (FISH) was performed as previously described (Olejniczak E T, Van Sant C, Anderson M G, et al: Integrative genomic analysis of small-cell lung carcinoma reveals correlates of sensitivity to bcl-2 antagonists and uncovers novel chromosomal gains. Mol Cancer Res 5:331-9, 2007) using a Vysis LSI Bcl-2® (orange) probe and chromosome 18 probe (green) developed by Abbott Molecular. Similar probes were used to assess Bcl-2 amplification in tumor biopsies. Pro-GRP was measured using ARCHITECT ELISA kits (Abbott Diagnostics, Abbott Park, Ill.). Serum samples were analyzed for M30 and M65 (Peviva) using previously described assays validated to good clinical laboratory practice (Cummings J, Ward T H, LaCasse E, et al: Validation of pharmacodynamic assays to evaluate the clinical efficacy of an antisense compound (AEG 35156) targeted to the X-linked inhibitor of apoptosis protein XIAP. Br J Cancer 92:532-8, 2005; and Cummings J, Ranson M, Lacasse E, et al: Method validation and preliminary qualification of pharmacodynamic biomarkers employed to evaluate the clinical efficacy of an antisense compound (AEG35156) targeted to the X-linked inhibitor of apoptosis protein XIAP. Br J Cancer 95:42-8, 2006).

Safety and Efficacy Assessments.

Subjects were evaluated with history, physical exam, vital signs, complete blood count, chemistries, urinalysis and ECOG PS weekly through C2 and on D1 of each subsequent cycle. ECG and 2D-ECHO were obtained on C1D-3, C1D14, C3D1, C3D14, and end of study. Platelet counts were obtained on D-3 through 14 of C1, and weekly through each subsequent cycle. Lymphocyte enumeration was performed at screening, C1D14, at the end of C4, and at the end of every $3^{rd}$ cycle thereafter. Radiographic tumor assessments were performed at baseline, after the $2^{nd}$ and $4^{th}$ cycles and after every 3 cycles thereafter.

Statistical Analyses.

This study was designed using an adaptation of the continual reassessment method (CRM) for dose escalation (Piantadosi S, Fisher J D, Grossman S: Practical implementation of a modified continual reassessment method for dose-finding trials. Cancer Chemother Pharmacol 41:429-36, 1998; O'Quigley J, Shen L Z: Continual reassessment method: a likelihood approach. Biometrics 52:673-84, 1996; Goodman S N, Zahurak M L, Piantadosi S: Some practical improvements in the continual reassessment method for phase I studies. Stat Med 14:1149-61, 1995, each fully incorporated by reference herein). A statistical model for dose assessment of toxicity including the accumulating data was used to guide selection of the next dose. Descriptive statistics summarized the demographics, safety data, and pharmacokinetics. Correlations between median Bcl-2 copy number, pro-GRP, M30, dose and best tumor response were made using the JMP 8.0 statistical software.

Results:

47 subjects were enrolled between April 2007 and May 2008; 35 on intermittent and 12 on continuous dosing cohorts. Primary toxicities included dose and schedule-dependent thrombocytopenia, diarrhea, nausea, and fatigue. One subject had a confirmed partial response and 7 subjects had stable disease. One SCLC subject remained on study for 13 months and a second remains on study for more than 2 years. Pro-GRP was identified as a surrogate marker of Bcl-2 amplification which was tracked in circulating tumor cells prior to and during therapy.

Table 2 shows the baseline characteristics of this heavily-pretreated patient population, over 60% of whom had small cell or other neuroendocrine cancers. Nine subjects were considered unevaluable for response. The most common reasons for study discontinuation were radiographic progressive disease, declining performance status and withdrawal of consent.

TABLE 2

Baseline patient characteristics (n = 47).

| Dosing Schedule | |
|---|---|
| 14/21 day dosing | 35 |
| 21/21 day dosing | 12 |
| Median Age, years | 62 |
| Gender | |
| Male | 27 (57.4%) |
| Female | 20 (42.6%) |
| ECOG Performance Status | |
| 0 | 16 (34.8%) |
| 1 | 26 (56.5%) |
| 2 | 4 (8.7%) |
| Previous Therapies | |
| 1-2 regimens | 9 (19.1%) |
| >3 regimens | 38 (80.9%) |
| Tumor Type | |
| SCLC | 26 (55.3%) |
| Pulmonary Carcinoid | 3 (6.4%) |
| Other | 18 (38.3%) |

Of the 38 subjects who were evaluable for response, 7 had stable disease and one of these remained on study for 13 months. One subject had a partial response that has been sustained for over 26 months and remains on study. The bulk of subjects with disease control were small cell carcinoma or pulmonary carcinoid tumor subjects treated at the highest dose levels (FIG. 4). In FIG. 4, the best tumor percent change is defined as the maximum reduction/minimum increase from baseline in tumor load. For subjects having the best percent change from baseline at multiple cycles, the earliest cycle is labeled. Best tumor percent change from baseline for subject 336 is truncated at 100%. Note, however, for some subjects, a reduction in target lesions did not translate to response based on growth of new lesions.

Figure 5A:
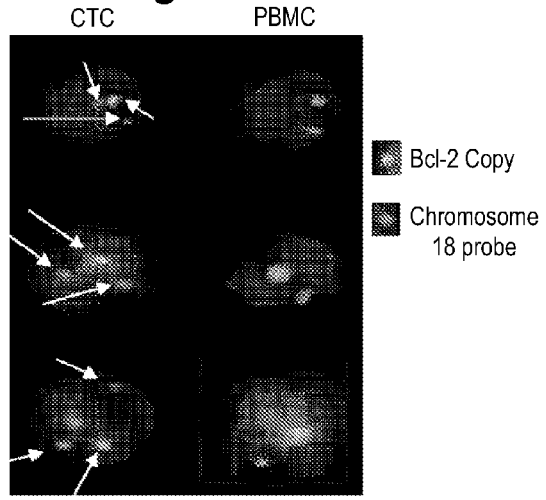
FIG. 5 shows biomarkers of navitoclax activity and tumor response. (A) FISH analysis of Bcl-2 (indicated by arrows) in CTC and PBMC. (B) Pro-GRP plasma concentration (pg/ml) plotted against mean Bcl-2 copy number. (C) Relative change in pro-GRP plasma concentration with different dose levels. (D) Best tumor percentage change plotted against percentage change of pro-GRP from baseline to cycle 2 day 14. (E) Changes in circulating M30 levels with increasing dose as measured in cycle 1, 6 hours post first exposure.
Figure 5B:
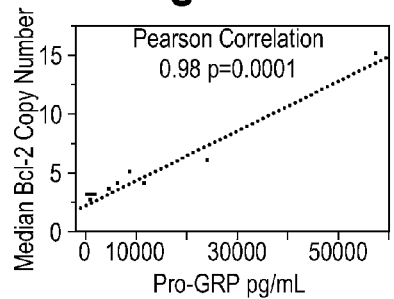
Figure 5C:
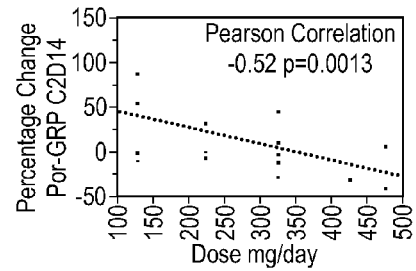
Figure 5D:
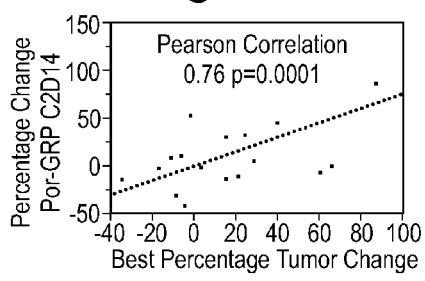
Figure 5E:
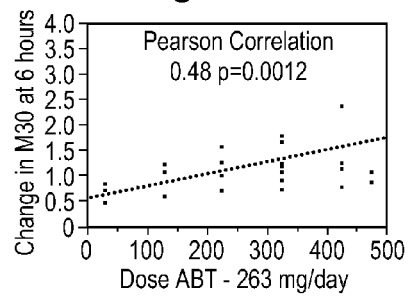

To determine whether Bcl-2 amplification was associated with response, Bcl-2 copy number was assessed in 46 subject blood samples subjected to CTC enumeration. Twenty-one subjects had 8 or more CTCs detected and in these, FISH for Bcl-2 was undertaken. FIG. 5A shows an example of a subject with amplification of Bcl-2 in CTCs, but not in peripheral blood mononuclear cells (PBMC). In subjects where Bcl-2 amplification could be undertaken, Bcl-2 copy number was compared to circulating pro-GRP levels. FIG. 5B shows a direct correlation between median Bcl-2 copy number circulating pro-GRP($R^2$=0.98), consistent with previous studies demonstrating co-amplification of these two genes. When only subjects with SCLC or neuroendocrine tumors were analyzed, the same correlation was seen ($R^2$=0.95, data not shown). Pro-GRP levels overall declined or stabilized with increasing navitoclax dose (FIG. 5C), but more importantly, the change in pro-GRP levels correlated with best percentage tumor change (FIG. 5D) ($R^2$=0.76). As another potential surrogate marker for navitoclax activity in promoting apoptosis, levels of caspase-cleaved CK18, an epithelial cell marker, were assessed with an antibody specific for the cleaved product, M30. M30 has previously been evaluated a potential serum biomarker for tumor cell death as it released only during apoptosisis and is specific for epithelial cells (Kramer G, Erdal H, Mertens H J, et al: Differentiation between cell death modes using measurements of different soluble forms of extracellular cytokeratin 18. Cancer Res 64:1751-6, 2004; and Hou J M, Greystoke A, Lancashire L, et al: Evaluation of circulating tumor cells and serological cell death biomarkers in small cell lung cancer patients undergoing chemotherapy. Am J Pathol 175:808-16, 2009). A dose-dependent transient increase in circulating M30 was observed at all dose cohorts apart from at 6 hours post dose ($R^2$=0.48, p=0.0012; FIG. 5E). In most instances, the rise in M30 rose rapidly within 6 hours following the first dose and apoptosis was sustained through 14 days of oral dosing, mirroring the biomarker behavior in a SCLC human xenograft preclinical model (Micha D, Cummings J, Shoemaker A, et al: Circulating biomarkers of cell death after treatment with the BH-3 mimetic ABT-737 in a preclinical model of small-cell lung cancer. Clin Cancer Res 14:7304-10, 2008).

This data demonstrates that navitoclax is safe, well-tolerated, with dose-dependent thrombocytopenia as the major side effect. Preliminary efficacy data are encouraging in SCLC and other neuroendocrine carcinomas. Efficacy in SCLC and the utility of pro-GRP and other biomarkers as an indicator/predictor of treatment response is evaluated in the following Example 4.

Example 4

The above Example 3 detailed the phase 1 portion of this study which was open to patients with all solid tumors. Observations from the phase 1 portion of the study provided confirmation of rapid and dose-dependent thrombocytopenia, a plasma half-life of approximately 15 hours, and preliminary evidence of anti-cancer activity including a durable partial response in a patient with SCLC (Example 3; also Gandhi L., et al., J Clin Oncol 29:909-16, 2011). The gene encoding Pro-GRP is in close proximity to BCL2 on 18q21, and data from the phase 1 study suggested a correlation between BCL2 gene copy number and plasma pro-GRP levels, as well as between the percent change in pro-GRP over the first 14 days of continuous treatment and reduction in tumor size. Exploration of doses and schedules in phase I suggested a recommended phase 2 dose of 325 mg daily.

The dosing and scheduling regimen from the phase 1 study detailed above was expanded to a phase 2 study, and was limited to patients with relapsed or refractory SCLC. This example summarizes the clinical outcome data in this consistently treated cohort of SCLC patients, present confirmatory data regarding exploratory correlates from the phase 1, and extend these data to develop prognostic markers for SCLC (which have been identified in newly diagnosed SCLC patients) including cytokeratin 19 fragment antigen 21-1 (CYFRA 21-1), neuron-specific enolase (NSE), and circulating tumor cell (CTC).

Patient Population.

Eligible candidates for the phase 2 portion of this study (NCT00445198) were adults with histologically or cytologically confirmed SCLC, extensive stage, with progressive disease after at least one prior chemotherapy regimen (any number of prior therapies were allowed). Eligible patients had an Eastern Cooperative Oncology Group (ECOG) performance status of ≤1, and had adequate bone marrow, renal, and hepatic function. Patients were excluded if they had underlying or predisposing condition of bleeding (history of non-chemotherapy induced thrombocytopenia with bleeding within 1 year, active peptic ulcer or hemorrhagic esophagitis/gastritis, active immune thrombocytopenic purpura, etc.). This study was conducted according to the Declaration of Helsinki and with approval from Institutional Review Boards of all participating study sites. All participants provided written informed consent before participating.

Study Design.

The phase 2 component of this clinical trial was an open-label, single arm study of patients with recurrent and progressive SCLC after at least one prior therapy. Based on the dose and schedule determined in phase 1 (Example 3), patients were treated with navitoclax 150 mg daily for 1 week, and 325 mg daily thereafter. Cycle duration was defined as 21 days. Subjects could remain on therapy indefinitely, until disease progression or intolerable toxicity.

Safety Assessment.

Safety assessments included history and physical examinations, vital signs, ECOG performance status, AEs, blood chemistry and complete blood counts with differential. Safety assessments were performed at screening, weekly during cycle 1, and at the start of subsequent cycles. Adverse event severity was graded according to the National Cancer Institute Common Terminology Criteria for Adverse Events (NCI CTCAE), version 3.0 (Common Terminology Criteria for Adverse Events. Version 3.0. Available at NCI website for the cancer therapy evaluation program (CTEP). Relationships of adverse events to navitoclax (definitely, probably, possibly, unlikely, or unrelated) were assessed by the Principal Investigator at each site.

Efficacy Assessment.

Tumor response was assessed using RECIST after every 2 cycles of therapy (Therasse P, Arbuck S G, Eisenhauer E A, et al: New guidelines to evaluate the response to treatment in solid tumors. European Organization for Research and Treatment of Cancer, National Cancer Institute of the United States, National Cancer Institute of Canada. J Natl Cancer Inst 92:205-16, 2000). Additional efficacy variables included PFS and OS.

Pharmacodynamic Correlates.

Blood specimens for analyzing circulating tumor cells (CTC) were collected at screening, on day 14 of cycles 1 and 2, and at final study visit (for US patients only). Circulating tumor cell detection was performed as previously described, (Benson A B, Kindler H L, Jodrell D, et al: Phase 2 study of ABT-751 in patients with refractory metastatic colorectal carcinoma (CRC). J Clin Oncol 23:255s, 2005 (suppl; abstr 3537)) using the CellSearch system (Veridex, Raritan, N.J.). Samples enriched for CTC are removed from the Veridex cartridge after the imaging and enumeration, washed 1× in PBS, pelleted then resuspended in 100 μL PBS and dropped onto a positively charged slide (Biogenex, San Ramon, Calif.) and dried. The slides are then rinsed in $H_2O$ prior to imaging using the Carl Zeiss (Germany) or Bioview imaging systems (Tel Aviv, Israel), the CTC are identified and the locations recorded. Fluorescence in-situ hybridization (FISH) was performed as previously described (Olejniczak E T, Van Sant C, Anderson M G, et al: Integrative genomic analysis of small-cell lung carcinoma reveals correlates of sensitivity to bcl-2 antagonists and uncovers novel chromosomal gains. Mol Cancer Res 5:331-9, 2007) using a Vysis LSI Bcl-2® (orange) probe and chromosome 18 probe (green) developed by Abbott Molecular (Des Plaines, Ill.). The slides are then returned to the Zeiss or Bioview imaging systems and the previously identified CTC are assessed for DNA copy number.

Serum and plasma samples collected at the same intervals were stored at −70° C. or colder until analyzed for quantitative assessment of tumor markers. CYFRA 21-1 and Pro-GRP were measured using the automated ARCHITECT ELISA kits (Abbott Diagnostics, Abbott Park, Ill.) and NSE was measured in plasma using automated electrochemoluminescent assays on Elecsys 2010 (Roche Diagnostics, Germany). Serum samples were analyzed for M30 and M65 (Peviva AB, Sweden) using previously described assays validated to good clinical laboratory practice (see, Cummings J., et al., Br J Cancer 92:532-8, 2005; and Cummings J., et al., Br J Cancer 95:42-8, 2006). These determinants have been previously explored as diagnostic, prognostic, or predictive biomarkers in first line SCLC patients, but not in connection with patients undergoing second line therapeutic regimen (see discussion below and generally, Holdenrieder S., et al., Clin Cancer Res 14:7813-21, 2008; Molina R., et al., Tumour Biol 24:209-18, 2003; Molina R., et al., Tumour Biol 30:121-9, 2009; and Rudin C. M., et al., J Clin Oncol 29:1075-82, 2011).

Statistical Analysis.

All subjects enrolled were included in the analyses. Descriptive statistics were used to summarize demographic variables. Progression free survival and overall survival were computed using Kaplan-Meier methodology and 95% confidence intervals were provided. Progression free survival (PFS) was defined as the number of days from the date the subject started the study drug to the date the subject experienced an event of disease progression, or if progression was not experienced, then the date of death if the death occurred within 42 days (length of time between tumor assessments). Overall survival (OS) was defined as the number of days from the date the subject started the study drug to the date of the subject's death. A sample size of 40 subjects was chosen to provide approximately 16 chemosensitive disease and 16 chemoresistant disease, this sample size provided 90% confidence that the true response rate was within 20-25% of the observed response rate.

Correlations between median BCL2 copy number and pro-GRP were performed by the Pearson correlation; M30 and CTC change from baseline comparisons among Pro-GRP groups were performed by one-way ANOVA using the JMP 8.0 statistical software. Optimized thresholds for the tumor markers were obtained using BATTing (Bootstrapping and Aggregating Thresholds from Trees) method (See, e.g., Breiman L., Bagging Predictors. Machine Learning 26:123-140, 1996, fully incorporated herein by reference). Briefly, BATTing uses a tree-based model for threshold estimation. However, a single tree may be unstable and not robust enough against small perturbations in the distribution of the data. In addition, single tree-based models are known be prone to overfitting (that is, it is over-specified for training data) and have poor prediction power. Those issues are addressed in BATTing by aggregating the thresholds from multiple trees to get a more robust estimate. Each tree is built using a bootstrap random sample drawn from the original population and provides its own cutoff. The final estimate of the threshold is calculated as the median from the distribution of cutoffs generated from the multiple trees. This procedure was implemented using the R statistical software (available online from the R project).

Results

Patient Characteristics and Study Drug Dosing.

A total of 39 patients participated in the phase 2 study. The majority of patients were of performance status 1. The median number of prior therapeutic regimens was 2 (range 1-6). A summary of patient demographics is shown in Table 4. All patients were started at the planned dose and schedule, including dose escalation to 325 mg in week 2. The primary reasons for study discontinuation included disease progression (N=26, 67%) and AEs (N=11, 28%). The median number of treatment cycles was 2 (range, 1-11) and the median treatment duration was 1.3 months (range, 0.2-7.3).

TABLE 4

Patient Demographics

| Demographic category | | N = 39 |
|---|---|---|
| Median age (range) | | 64 (45-78) |
| Female, n (%) | | 21 (54) |
| ECOG PS, n (%) | 0 | 13 (33) |
| | 1 | 25 (64) |
| | (missing) | 1 (3) |
| Prior therapeutic regimens | 1-2 | 28 (72) |
| | ≥3 | 11 (28) |

Efficacy.

Figure 6:
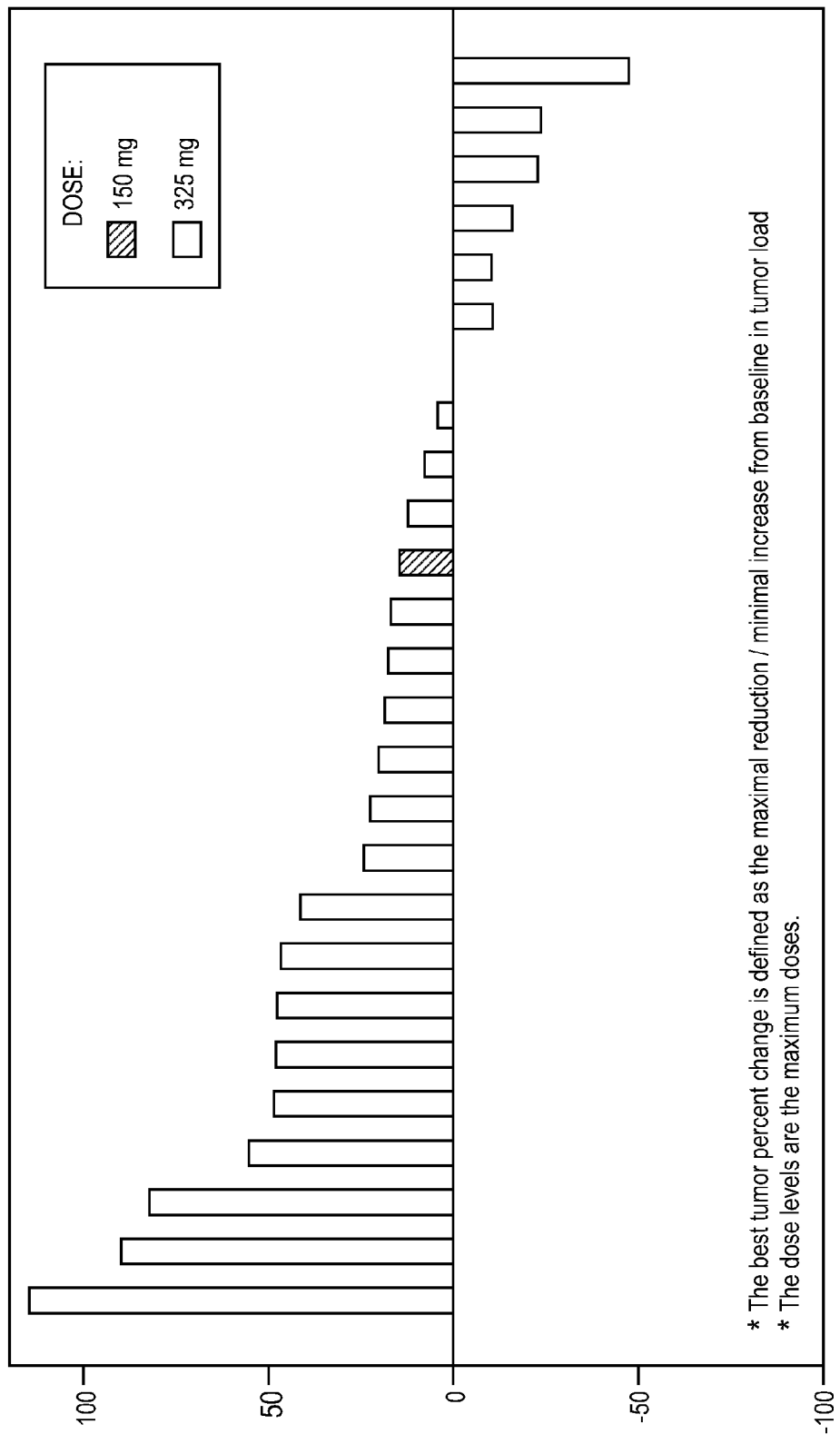
FIG. 6 shows a waterfall plot of best fractional change in tumor size relative to baseline. The best tumor size % change from baseline is defined as the maximal reduction or minimal increase in sum of longest dimensions of target lesions relative to pretreatment assessment.

A waterfall plot representing best % change from baseline in identified target lesions is shown in FIG. 6. Only one confirmed partial response (PR) was observed (2.6%). Nine patients (23.1%) experienced stable disease (SD) as best response. Sixteen patients (41%) had a best response of disease progression (PD), and another 13 (33.3%) were inevaluable for response. These 13 did not complete 2 cycles of therapy, and did not have post-treatment tumor assessments on protocol. Median progression-free survival (PFS) was 1.5 months (95% CI 1.4-1.7) and median overall survival (OS) 3.2 months (95% CI 2.3-8.1). See, Table 5.

TABLE 5

Efficacy data summary

| Efficacy endpoint | Patients (N = 39) |
|---|---|
| Median PFS, mo (95% CI) | 1.5 (1.4, 1.7) |
| Median OS, mo (95% CI) | 3.2 (2.3, 8.1) |
| ORR, % (95% CI) | 2.6 (0.1, 13.5) |
| Best response, N (%) | |
| PR | 1 (2.6) |
| SD | 9 (23.1) |
| PD | 16 (41.0) |
| inevaluable* | 13 (33.3) |

PFS = progression-free survival;
OS = overall survival;
CI = confidence interval
ORR = overall response rate
*Baseline tumor data only.

Pharmacodynamic Correlates.

Several exploratory correlative biomarkers were included in this study, including both CTC enumeration and plasma protein markers associated with small cell lung cancer. The biomarker analysis included all phase II patients and, to increase the sample size, patients with SCLC and those dosed with >325 mg navitoclax on the phase I portion of this study were also included in the analysis. Biomarkers correlating with outcome that are assessable prior to treatment are of particular potential utility, consequently we determined optimized thresholds prognostic for patient outcome using BATTing for several tumor markers including CYFRA 21.1, NSE, and CTC at baseline and on cycle 1 day 14. A summary of pretreatment biomarkers evaluated are presented in Table 6. Interestingly, baseline levels of CTC, and of both plasma biomarkers, appear to be associated with both PFS and OS in patients treated with navitoclax. CTC levels at cycle 1 day 14 were also significantly associated with outcome (data not shown).

TABLE 6

Biomarker thresholds

| Baseline biomarker | Threshold | Median PFS | | | Median OS | | |
|---|---|---|---|---|---|---|---|
| | | Above threshold D (N) | Below threshold D (N) | p-value | Above threshold D (N) | Below threshold D (N) | p-value |
| CYFRA 21.1 | 2.3 ng/ml | 44 (19) | 53 (20) | 0.0045 | 67 (19) | 242 (20) | 0.0052 |
| NSE | 15 ng/ml | 44 (24) | 55 (15) | 0.0334 | 72 (24) | 242 (15) | 0.1208 |
| CTC | 12/7.5 ml | 46 (15) | 63 (14) | 0.0045 | 67 (17) | NR (14) | 0.004 |

D = days; N = number of patients; CYFRA = cytokeratin-19 fragment; NSE = neuron-specific enolase; CTC = circulating tumor cells; NR = not reached.

Figure 7A:
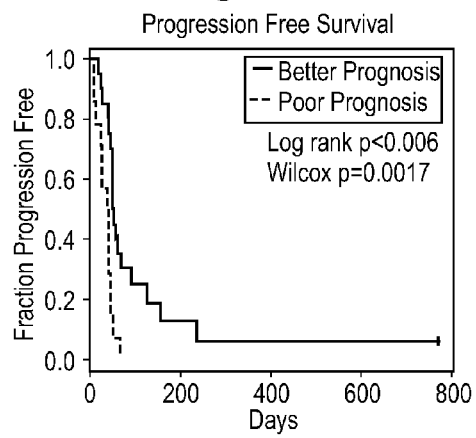
FIG. 7 shows pharmacodynamic biomarker assessment. NSE and CYFRA threshold prognosis assessed by progression-free survival (A) and overall survival (B). High plasma Pro-GRP (correlating with BCL2 gene amplification) associated apoptosis as assessed by the M30 ELISA assay (C), plasma Pro-GRP concentration effect on CTC from baseline to day 14 (D).
Figure 7B:
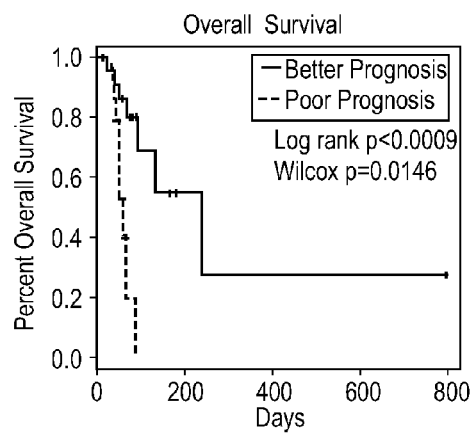

By grouping patients above these thresholds for both NSE and CYFRA in the analysis, we identified a population of patients with poor prognosis (median PFS: 41 days [n=16] vs 55 days [n=23], FIG. 7A, p=0.0006; median OS: 61 days [n=15] vs 242 days [n=18], FIG. 7B, p=0.0009). The elimination of this population from the analysis further identified a subset of patients with more favorable outcomes and allowed us to assess the impact of navitoclax on a variety of patient response biomarkers.

For the better prognosis patients the breakout is
NSE high/CYFRA low=8
NSE low/CYFRA high=3
NSE low/CYFRA low=12.

Pro-GRP was of particular interest with regard to navitoclax, as the GRP gene is in close chromosomal proximity to BCL2, the gene encoding the primary target for this drug. BCL2 copy number correlates with relative sensitivity to navitoclax in small cell lung cancer cell lines. Plasma pro-GRP levels may correlate with tumor BCL2 copy number, and were implicated in our phase I study (Example 3) as a relatively non-invasive means of assessing tumor BCL2 gene amplification. To further evaluate this association, we assessed plasma Pro-GRP, and BCL2 copy number by FISH in CTC from patients on this study (n=10). A strong correlation was confirmed (Pearson correlation 0.93, p<0.0001). We identified an optimal Pro-GRP threshold linked with amplification of Bcl-2 at 600 pg/mL and compared the activity of navitoclax between patients above and below this threshold using two measurements of activity. First, examining only the better prognosis patients as they are the most likely to be healthy enough to benefit from treatment with navitoclax, we examined the early activation of the apoptotic pathway in patient serum, with the M30 ELISA assay. This assay measures the release of caspase-cleaved cytokeratin 18 following apoptotic cell death. M30 concentrations were significantly increased in patients in the high Pro-GRP group when compared to those with low Pro-GRP (205% vs 116%, FIG. 7C, p=0.0079). In addition, we examined the changes in CTC levels, as a potential marker of disease progression and found that the median CTC number increased in the low pro-GRP group by 349% of baseline, but not in the high pro-GRP group (91% of baseline, FIG. 7D, p=0.0451). By comparison, when we examined the changes in the total population the differences between the Pro-GRP groups were still statistically significant but with a reduced magnitude of difference.

Figure 7C:
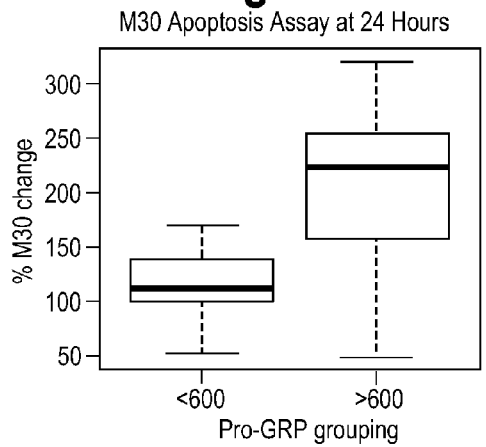
Figure 7D:
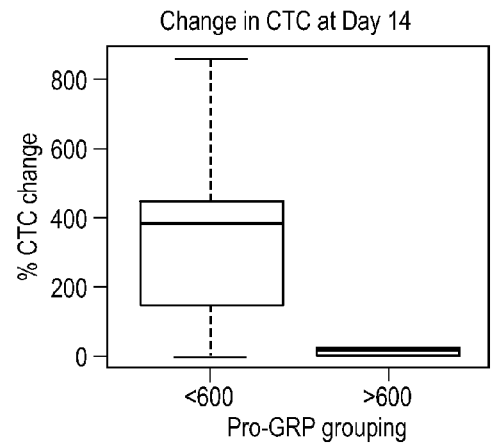

M30 concentrations were significantly increased in patients in the high Pro-GRP group n=19 when compared to those with low Pro-GRP n=13 (212% vs 109%, FIG. 7C, p=0.0178). In addition, we examined the changes in CTC levels and found that the median CTC number increased more in the low pro-GRP group n=8 by 518% of baseline, than in the high pro-GRP group n=12 (186% of baseline, FIG. 7D, p=0.0433).

The correlative biomarkers and thresholds described herein can be used in future clinical evaluation in SCLC. Some of these endpoints, such as CTC enumeration and tumor marker expression, could potentially serve as prognostic biomarkers, associated with poor outcome across a variety of therapeutic strategies and in a variety of clinical contexts. While baseline levels of CYFRA 21-1, NSE, pro-GRP, and circulating tumor cell number have been explored as prognostic markers for newly diagnosed SCLC, these first-line patients have predominantly been treated with platinum containing regimens. For example, Holdenrieder et al (Clin Cancer Res 14:7813-21, 2008) have identified high levels of CYFRA 21-1 at baseline and high levels of CYFRA 21-1 and NSE on therapy as poor prognostic markers in first line SCLC patients. Bremnes et al., (Lung Cancer 39: 303-313, 2003) have demonstrated that higher concentrations of NSE are a poor prognostic factor in uni- and multivariate analysis using the Cox regression model, Ando et al., (ANTICANCER RESEARCH 24: 1941-1946, 2004) demonstrated that concentrations above a diagnostic threshold for NSE and CYFRA 21-1 were individually poorly prognostic in newly diagnosed SCLC patients with hazard ratios (HR) for OS of 3.9 and 2.6 respectively, and that patients above the threshold for both markers had an even higher HR of 10.25 in multivariate analysis. Hou et al., (American Journal of Pathology, 175: 808-16, 2009) have demonstrated that higher concentrations of total cytokeratin 18 and circulating tumor cells at baseline and caspase cleaved cytokeratin 18 (M30) and CTC at day 22 were predictive of poor outcome in first line therapy.

The data gathered from our phase 1 and phase 2 studies demonstrate that these markers are prognostic in second line therapy using Bcl-2 inhibitors, such as navitoclax and the related compound ABT-737, and provide useful threshold levels for prognosis and classification of patients as likely or unlikely candidates for therapeutic intervention with such compounds. Certain biomarkers, such as plasma pro-GRP, may reflect tumor dependence on Bcl-2, and could prove to be more closely linked to activity of potent and specific Bcl-2 inhibitors. These biomarkers can be incorporated into existing and future clinical trials such as, for example, in patients with SCLC and will allow for further validation and refinement of their utility as prognostic markers for SCLC as well as predictive markers for treatment with Bcl-2 inhibitor compounds such as navitoclax.

We claim:

1. A method for classifying a patient having cancer as a candidate for therapy with a Bcl-2 family inhibitor comprising:
   (a) providing a tissue, blood, plasma or serum sample from a patient;
   (b) determining the level of (i) plasma pro-gastrin releasing peptide (proGRP), (ii) cytokeratin 19 fragment antigen 21-1 (CYFRA 21-1), (iii) neuron-specific enolase (NSE), (iv) circulating tumor cell (CTC) number, and (v) Bcl-2 gene copy number in the tissue, blood, plasma or serum sample;
   (c) classifying the patient as a candidate for therapy with the Bcl-2 family inhibitor when the tissue, blood, plasma or serum sample is determined as having an increased level, relative to a threshold level, of (i) plasma pro-gastrin releasing peptide (pro-GRP) and (v) Bcl-2 gene copy number; and a decreased level, relative to a threshold level, of (ii) cytokeratin 19 fragment antigen 21-1 (CYFRA 21-1), (iii) neuron-specific enolase (NSE), and (iv) circulating tumor cell (CTC) number; and
   (d) administering the Bcl-2 family inhibitor to the patient classified in step (c) as a candidate for therapy with the Bcl-2 family inhibitor, wherein the Bcl-2 family inhibitor is N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl-)propyl)amino)-3-((trifluoromethyl)sulfonyl)benzenesulfonamide(navitoclax),
   wherein (i) the plasma pro-GRP threshold level is about 600 pg/mL, (ii) the CYFRA 21-1 threshold level is about 2.3 ng/mL, (iii) the NSE threshold level is about 15 ng/mL, (iv) the CTC number threshold level is about 12 per 7.5 mL, and (v) Bcl-2 gene copy number is greater than 2.

2. The method of claim 1, wherein the tissue, blood, plasma or serum sample is from a patient with a cancer selected from the group consisting of small cell lung carcinoma (SCLC) and a solid tumor cancer.

3. The method of claim 1, wherein the tissue, blood, plasma or serum sample is from a patient with a relapsed or refractory cancer selected from the group consisting of small cell lung carcinoma (SCLC) and a solid tumor cancer.

4. The method of claim 1, wherein the tissue, blood, plasma or serum sample is from a patient with a relapsed or refractory cancer selected from the group consisting of solid tumor cancer, squamous cell cancer (e.g., epithelial squamous cell cancer), lung cancer including small-cell lung cancer, non-small cell lung cancer, adenocarcinoma of the lung and squamous carcinoma of the lung, esophageal cancer, prostate cancer, cancer of the peritoneum, hepatocellular cancer, gastric or stomach cancer including gastrointestinal cancer, neuroendocrine cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, melanoma, multiple myeloma and B-cell lymphoma, brain, head and neck cancer, and associated metastases.

5. The method of claim 1, wherein the tissue, blood, plasma or serum sample comprises a peripheral blood sample, a tumor or suspected tumor tissue, a thin layer cytological sample, a fine needle aspirate sample, a bone marrow sample, a lymph node sample, a urine sample, an ascites sample, a lavage sample, an esophageal brushing sample, a bladder or lung wash sample, a spinal fluid sample, a brain fluid sample, a ductal aspirate sample, a nipple discharge sample, a pleural effusion sample, a fresh frozen tissue sample, a paraffin embedded tissue sample or an extract or processed sample produced from any of a peripheral blood sample, a serum or plasma fraction of a blood sample, a tumor or suspected tumor tissue, a thin layer cytological sample, a fine needle aspirate sample, a bone marrow sample, a lymph node sample, a urine sample, an ascites sample, a lavage sample, an esophageal brushing sample, a bladder or lung wash sample, a spinal fluid sample, a brain fluid sample, a ductal aspirate sample, a nipple discharge sample, a pleural effusion sample a fresh frozen tissue sample or a paraffin embedded tissue sample.

6. The method of claim 1, wherein the determining step (b) is performed by immunoassay to a peripheral blood sample or plasma or serum fraction thereof.

7. A method for classifying a patient having cancer as a candidate for second-line therapy with a Bcl-2 family inhibitor comprising:
   (a) providing a tissue, blood, plasma or serum sample from a patient;
   (b) determining the level of (i) plasma pro-gastrin releasing peptide (proGRP), (ii) cytokeratin 19 fragment antigen 21-1 (CYFRA 21-1), (iii) neuron-specific enolase (NSE), (iv) circulating tumor cell (CTC) number, and (v) Bcl-2 gene copy number in the tissue, blood, plasma or serum sample;
   (c) classifying the patient as a candidate for second-line therapy with the Bcl-2 family inhibitor when the tissue, blood, plasma or serum sample is determined as having an increased level, relative to a threshold level, of (i) plasma pro-gastrin releasing peptide (pro-GRP) and (v) Bcl-2 gene copy number; and a decreased level, relative to a threshold level, of (ii) cytokeratin 19 fragment antigen 21-1 (CYFRA 21-1), (iii) neuron-specific enolase (NSE), and (iv) circulating tumor cell (CTC) number; and
   (d) administering the Bcl-2 family inhibitor to the patient classified in step (c) as a candidate for second-line therapy with the Bcl-2 family inhibitor, wherein the Bcl-2 family inhibitor is N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenyl-sulfanyl)methyl-)propyl)amino)-3-((trifluoromethyl)sulfonyl)benzenesulfonamide(navitoclax),
   wherein (i) the plasma pro-GRP threshold level is about 600 pg/mL, (ii) the CYFRA 21-1 threshold level is about 2.3 ng/mL, (iii) the NSE threshold level is about 15 ng/mL, (iv) the CTC number threshold level is about 12 per 7.5 mL, and (v) Bcl-2 gene copy number is greater than 2.

8. The method of claim 7, wherein the tissue, blood, plasma or serum sample is from a patient with a relapsed or refractory cancer selected from the group consisting of solid tumor cancer, squamous cell cancer (e.g., epithelial squamous cell cancer), lung cancer including small-cell lung cancer, non-small cell lung cancer, adenocarcinoma of the lung and squamous carcinoma of the lung, esophageal cancer, prostate cancer, cancer of the peritoneum, hepatocellular cancer, gastric or stomach cancer including gastrointestinal cancer, neuroendocrine cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, melanoma, multiple myeloma and B-cell lymphoma, brain, head and neck cancer, and associated metastases.

9. The method of claim 7, wherein the determining step (b) is performed by immunoassay to a peripheral blood sample or plasma or serum fraction thereof.

* * * * *